US012700478B2

(12) United States Patent　　(10) Patent No.:　US 12,700,478 B2
Yao et al.　　(45) Date of Patent:　Aug. 4, 2026

(54) SEQUENCING DATA-ENCODED PEPTIDES FROM TANDEM MASS SPECTRA

(71) Applicant: THE HONG KONG POLYTECHNIC UNIVERSITY, Hong Kong (CN)

(72) Inventors: Zhongping Yao, Hong Kong (CN); Cheuk Chi Ng, Hong Kong (CN); Francis Chung Ming Lau, Hong Kong (CN); Wai Man Tam, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 594 days.

(21) Appl. No.: 18/297,685

(22) Filed: Apr. 10, 2023

(65) Prior Publication Data

US 2023/0326558 A1　　Oct. 12, 2023

Related U.S. Application Data

(60) Provisional application No. 63/362,757, filed on Apr. 11, 2022.

(51) Int. Cl.
　*G16B 50/30*　　(2019.01)
　*C12Q 1/68*　　(2018.01)
　(Continued)

(52) U.S. Cl.
　CPC .............. *G16B 50/30* (2019.02); *C12Q 1/68* (2013.01); *G01N 33/68* (2013.01); *G06F 16/215* (2019.01); *G06F 16/9024* (2019.01); *G16B 40/10* (2019.02)

(58) Field of Classification Search
None
See application file for complete search history.

(56) References Cited

U.S. PATENT DOCUMENTS 5,072,115 A　12/1991　Zhou
6,104,027 A　8/2000　Gee et al.
(Continued)

OTHER PUBLICATIONS

Ng, C. C. A., Tam, W. M., Yin, H., Wu, Q., So, P.-K., Wong, M. Y.-M., Lau, F. C. M., Yao, Z.-P., Data storage using peptide sequences. Nat. Commun., 2021, 12, 4242.
(Continued)

*Primary Examiner* — Walter L Lindsay, Jr.
*Assistant Examiner* — Geoffrey T Evans
(74) *Attorney, Agent, or Firm* — S&F/WEHRW

(57)　　ABSTRACT

Peptide sequencing is important in decoding data stored in a data-encoded peptide. Tandem mass spectrometry (MS/MS) is particularly useful for peptide sequencing. In a computer-implemented method for sequencing the data-encoded peptide from an experimental spectrum, raw data of the experimental spectrum are first preprocessed to remove uninterpretable peaks to yield preprocessed data. A first set of one or more candidate sequences contending for a peptide sequence of the peptide is identified from a spectrum graph. The spectrum graph is formed according to the preprocessed data rather than the raw data for generating a fewer number of candidate sequences to thereby reduce a time cost in sequencing. The first candidate-sequence set is then processed to estimate the peptide sequence to thereby obtain a set of peptide-sequence estimate(s). Each estimate is verified whether it is invalid. The set of peptide-sequence estimate(s) is purged to remove any invalid estimate.

18 Claims, 13 Drawing Sheets

Specification includes a Sequence Listing.

(51) Int. Cl.
  *G01N 33/68*    (2006.01)
  *G06F 16/215*    (2019.01)
  *G06F 16/901*    (2019.01)
  *G16B 40/10*    (2019.01)

(56)      References Cited

U.S. PATENT DOCUMENTS

| | | | |
|---|---|---|---|
| 11,315,023 | B2 | 4/2022 | Yao et al. |
| 2021/0090688 | A1 | 3/2021 | Yao et al. |

OTHER PUBLICATIONS

Mo, L. J., Dutta, D., Wan, Y. H., Chen, T., MSNovo: a dynamic programming algorithm for de novo peptide sequencing via tandem mass spectrometry. Anal. Chem. 2007, 79, 4870-4878.

Frank, A., Pevzner, P., PepNovo: De novo peptide sequencing via probabilistic network modeling. Anal. Chem. 2005, 77, 964-973.

Jeong, K., Kim, S., Pevzner, P. A., UniNovo: a Universal Tool for de Novo Peptide Sequencing. RECOMB., 2013.

Chi, H., Chen, H., He, K., Wu, L., Yang, B., Sun, R., Liu, J., Zeng, W., Song, C., He, S., Dong, M., pNovo+: de novo peptide sequencing using complementary HCD and ETD tandem mass spectra. J. Proteome Res., 2013, 12, 615-625.

Ma, B., Zhang, K., Hendrie, C., Liang, C., Li, M., Doherty-Kirby, A., Lajoie, G., PEAKS: powerful software for peptide de novo sequencing by tandem mass spectrometry. Rapid Commun. Mass Spectrom. 2003, 17, 2337-42.

Ma B., Novor: real-time peptide de novo sequencing software. J. Am. Soc. Mass. Spectrom. 2015, 26, 1885-94.

Extended European Search Report of EP23167234.6 issued from the European Patent Office on Sep. 11, 2023.

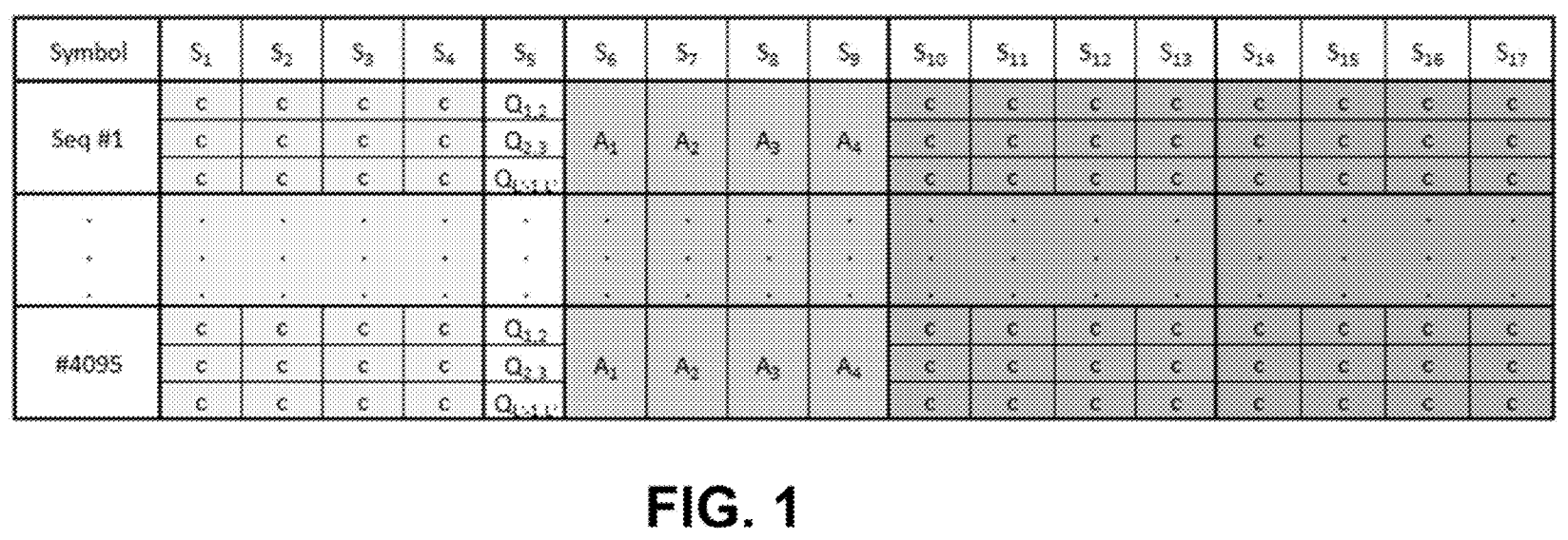

| Symbol | $S_1$ | $S_2$ | $S_3$ | $S_4$ | $S_5$ | $S_6$ | $S_7$ | $S_8$ | $S_9$ | $S_{10}$ | $S_{11}$ | $S_{12}$ | $S_{13}$ | $S_{14}$ | $S_{15}$ | $S_{16}$ | $S_{17}$ |
|---|---|---|---|---|---|---|---|---|---|---|---|---|---|---|---|---|---|
| Seq #1 | c | c | c | c | $Q_{1,2}$ $Q_{2,3}$ $Q_{1,2,3,4}$ | $A_1$ | $A_2$ | $A_3$ | $A_4$ | c | c | c | c | c | c | c | c |
| · · · | · | · | · | · | · · · | · | · | · | · | · | · | · | · | · | · | · | · |
| #4095 | c | c | c | c | $Q_{1,2}$ $Q_{2,3}$ $Q_{1,2,3,4}$ | $A_1$ | $A_2$ | $A_3$ | $A_4$ | c | c | c | c | c | c | c | c |

FIG. 1

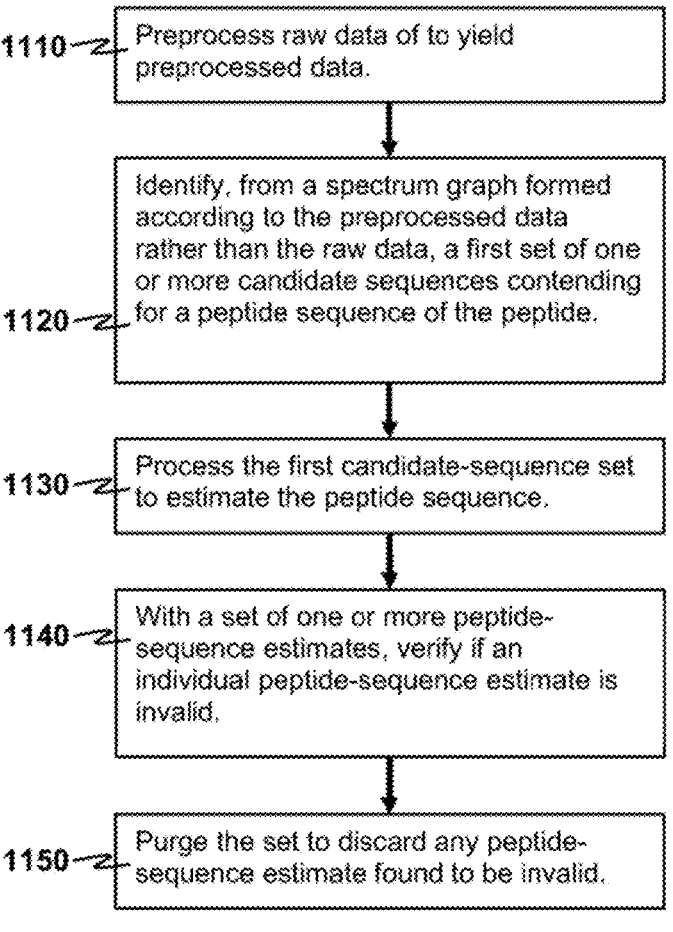

1110 — Preprocess raw data of to yield preprocessed data.

1120 — Identify, from a spectrum graph formed according to the preprocessed data rather than the raw data, a first set of one or more candidate sequences contending for a peptide sequence of the peptide.

1130 — Process the first candidate-sequence set to estimate the peptide sequence.

1140 — With a set of one or more peptide-sequence estimates, verify if an individual peptide-sequence estimate is invalid.

1150 — Purge the set to discard any peptide-sequence estimate found to be invalid.

1210 — Divide m/z ratios of raw data into subsets each for isotopes of a fragment.

1220 — Compute monoisotopic mass of the fragment for each subset.

1230 — Compute intensity of the fragment for each subset.

1240 — Distribute the masses into mass sets of putative b-ions and of putative y-ions.

1250 — Generate the preprocessed data, including (monoisotopic) masses, intensities, etc.

1110

SEQUENCE LISTING

```
Sequence total quantity: 50
SEQ ID NO: 1            moltype = AA  length = 17
FEATURE                Location/Qualifiers
source                 1..17
                       mol_type = protein
                       organism = synthetic construct
SEQUENCE: 1
FGFVSEYYYY TVGSTAR                                              17

SEQ ID NO: 2            moltype = AA  length = 18
FEATURE                Location/Qualifiers
source                 1..18
                       mol_type = protein
                       organism = synthetic construct
SEQUENCE: 2
FFEYGGYYYT SYFGYEGR                                             18

SEQ ID NO: 3            moltype = AA  length = 19
FEATURE                Location/Qualifiers
source                 1..19
                       mol_type = protein
                       organism = synthetic construct
SEQUENCE: 3
FTFVYEYYYE YVYVYFEAR                                            19
```

-continued

```
SEQ ID NO: 4            moltype = AA   length = 20
FEATURE                 Location/Qualifiers
source                  1..20
                        mol_type = protein
                        organism = synthetic construct
SEQUENCE: 4
FVAVLVYYYV SSETVLFGER                                        20

SEQ ID NO: 5            moltype = AA   length = 21
FEATURE                 Location/Qualifiers
source                  1..21
                        mol_type = protein
                        organism = synthetic construct
SEQUENCE: 5
FYTFGYYYYA GFTFTTESYA R                                      21

SEQ ID NO: 6            moltype = AA   length = 17
FEATURE                 Location/Qualifiers
source                  1..17
                        mol_type = protein
                        organism = synthetic construct
SEQUENCE: 6
FEYFESYYYS VVAGFFR                                           17

SEQ ID NO: 7            moltype = AA   length = 18
FEATURE                 Location/Qualifiers
source                  1..18
                        mol_type = protein
                        organism = synthetic construct
SEQUENCE: 7
FVLVVEYYYG GGSTSTFR                                          18

SEQ ID NO: 8            moltype = AA   length = 19
FEATURE                 Location/Qualifiers
source                  1..19
                        mol_type = protein
                        organism = synthetic construct
SEQUENCE: 8
FSFAAEYYYF FETYSFEFR                                         19

SEQ ID NO: 9            moltype = AA   length = 20
FEATURE                 Location/Qualifiers
source                  1..20
                        mol_type = protein
                        organism = synthetic construct
SEQUENCE: 9
FTYEVSYYTY FYSTGSAGAR                                        20

SEQ ID NO: 10           moltype = AA   length = 21
FEATURE                 Location/Qualifiers
source                  1..21
                        mol_type = protein
                        organism = synthetic construct
SEQUENCE: 10
FFTFTSYYTT ASAGGTVEAE R                                      21

SEQ ID NO: 11           moltype = AA   length = 17
FEATURE                 Location/Qualifiers
source                  1..17
                        mol_type = protein
                        organism = synthetic construct
SEQUENCE: 11
FEFVTVYYTE AATAAYR                                           17

SEQ ID NO: 12           moltype = AA   length = 18
FEATURE                 Location/Qualifiers
source                  1..18
                        mol_type = protein
                        organism = synthetic construct
SEQUENCE: 12
FALVTVYYTV AYGASSER                                          18

SEQ ID NO: 13           moltype = AA   length = 19
FEATURE                 Location/Qualifiers
source                  1..19
                        mol_type = protein
                        organism = synthetic construct
SEQUENCE: 13
FVTTYFYYTA EFSEASEYR                                         19
```

-continued

```
SEQ ID NO: 14             moltype = AA  length = 20
FEATURE                   Location/Qualifiers
source                    1..20
                          mol_type = protein
                          organism = synthetic construct
SEQUENCE: 14
FYVGFTYYTS VAFFFEYFAR                                              20

SEQ ID NO: 15             moltype = AA  length = 21
FEATURE                   Location/Qualifiers
source                    1..21
                          mol_type = protein
                          organism = synthetic construct
SEQUENCE: 15
FFYGTAYYTG VVFVFYAVYV R                                            21

SEQ ID NO: 16             moltype = AA  length = 17
FEATURE                   Location/Qualifiers
source                    1..17
                          mol_type = protein
                          organism = synthetic construct
SEQUENCE: 16
FTTSTAYYTF YTFTVFR                                                17

SEQ ID NO: 17             moltype = AA  length = 18
FEATURE                   Location/Qualifiers
source                    1..18
                          mol_type = protein
                          organism = synthetic construct
SEQUENCE: 17
FFYAESYYEY LEYVVFER                                               18

SEQ ID NO: 18             moltype = AA  length = 19
FEATURE                   Location/Qualifiers
source                    1..19
                          mol_type = protein
                          organism = synthetic construct
SEQUENCE: 18
FGEAYSYYET SGFFVYGVR                                              19

SEQ ID NO: 19             moltype = AA  length = 20
FEATURE                   Location/Qualifiers
source                    1..20
                          mol_type = protein
                          organism = synthetic construct
SEQUENCE: 19
FTAYTEYYEE SSSSFAETGR                                             20

SEQ ID NO: 20             moltype = AA  length = 21
FEATURE                   Location/Qualifiers
source                    1..21
                          mol_type = protein
                          organism = synthetic construct
SEQUENCE: 20
FFFAEFYYEV TFESEYEGGE R                                           21

SEQ ID NO: 21             moltype = AA  length = 17
FEATURE                   Location/Qualifiers
source                    1..17
                          mol_type = protein
                          organism = synthetic construct
SEQUENCE: 21
FSVETGYYEA YGEEYTR                                                17

SEQ ID NO: 22             moltype = AA  length = 18
FEATURE                   Location/Qualifiers
source                    1..18
                          mol_type = protein
                          organism = synthetic construct
SEQUENCE: 22
FVFEFEYYES YYEYAVAR                                               18

SEQ ID NO: 23             moltype = AA  length = 19
FEATURE                   Location/Qualifiers
source                    1..19
                          mol_type = protein
                          organism = synthetic construct
SEQUENCE: 23
```

```
FVVGASYYEG YYASYSSER                                         19

SEQ ID NO: 24          moltype = AA  length = 20
FEATURE                Location/Qualifiers
source                 1..20
                       mol_type = protein
                       organism = synthetic construct
SEQUENCE: 24
FGAFGSYYEF EGVVTESAVR                                        20

SEQ ID NO: 25          moltype = AA  length = 21
FEATURE                Location/Qualifiers
source                 1..21
                       mol_type = protein
                       organism = synthetic construct
SEQUENCE: 25
FYEVAYYYVY YSVVTSLAYE R                                      21

SEQ ID NO: 26          moltype = AA  length = 17
FEATURE                Location/Qualifiers
source                 1..17
                       mol_type = protein
                       organism = synthetic construct
SEQUENCE: 26
FSTTSGYYVT FSYGEGR                                           17

SEQ ID NO: 27          moltype = AA  length = 18
FEATURE                Location/Qualifiers
source                 1..18
                       mol_type = protein
                       organism = synthetic construct
SEQUENCE: 27
FVAVAVYYVE FAVYYSYR                                          18

SEQ ID NO: 28          moltype = AA  length = 19
FEATURE                Location/Qualifiers
source                 1..19
                       mol_type = protein
                       organism = synthetic construct
SEQUENCE: 28
FYTAEYYYVV ESGESFYTR                                         19

SEQ ID NO: 29          moltype = AA  length = 20
FEATURE                Location/Qualifiers
source                 1..20
                       mol_type = protein
                       organism = synthetic construct
SEQUENCE: 29
FEETAFYYVA FGASAYVSAR                                        20

SEQ ID NO: 30          moltype = AA  length = 21
FEATURE                Location/Qualifiers
source                 1..21
                       mol_type = protein
                       organism = synthetic construct
SEQUENCE: 30
FYGVEEYYVS AVTTYSGEYF R                                      21

SEQ ID NO: 31          moltype = AA  length = 17
FEATURE                Location/Qualifiers
source                 1..17
                       mol_type = protein
                       organism = synthetic construct
SEQUENCE: 31
FFEVFSYYVG ATTSAYR                                           17

SEQ ID NO: 32          moltype = AA  length = 18
FEATURE                Location/Qualifiers
source                 1..18
                       mol_type = protein
                       organism = synthetic construct
SEQUENCE: 32
FETAFSYYVF FVEGFAVR                                          18

SEQ ID NO: 33          moltype = AA  length = 19
FEATURE                Location/Qualifiers
source                 1..19
                       mol_type = protein
                       organism = synthetic construct
```

-continued

```
SEQUENCE: 33
FSVASSYYAY ESTVYVAVR                                                  19

SEQ ID NO: 34          moltype = AA  length = 20
FEATURE                Location/Qualifiers
source                 1..20
                       mol_type = protein
                       organism = synthetic construct
SEQUENCE: 34
FGVEEFYYAT VVTYGGSSER                                                 20

SEQ ID NO: 35          moltype = AA  length = 21
FEATURE                Location/Qualifiers
source                 1..21
                       mol_type = protein
                       organism = synthetic construct
SEQUENCE: 35
FEEFYSYYAE SSGTFGAAVV R                                               21

SEQ ID NO: 36          moltype = AA  length = 17
FEATURE                Location/Qualifiers
source                 1..17
                       mol_type = protein
                       organism = synthetic construct
SEQUENCE: 36
FGYGVSYYAV TTESETR                                                    17

SEQ ID NO: 37          moltype = AA  length = 18
FEATURE                Location/Qualifiers
source                 1..18
                       mol_type = protein
                       organism = synthetic construct
SEQUENCE: 37
FEAAYEYYAA YTAGGEAR                                                   18

SEQ ID NO: 38          moltype = AA  length = 19
FEATURE                Location/Qualifiers
source                 1..19
                       mol_type = protein
                       organism = synthetic construct
SEQUENCE: 38
FAFEYEYYAS FAEVGTTVR                                                  19

SEQ ID NO: 39          moltype = AA  length = 20
FEATURE                Location/Qualifiers
source                 1..20
                       mol_type = protein
                       organism = synthetic construct
SEQUENCE: 39
FEVFYTYYAG AAAEFGGFER                                                 20

SEQ ID NO: 40          moltype = AA  length = 21
FEATURE                Location/Qualifiers
source                 1..21
                       mol_type = protein
                       organism = synthetic construct
SEQUENCE: 40
FLVATAYYAF VEYLVVVAES R                                               21

SEQ ID NO: 41          moltype = AA  length = 17
FEATURE                Location/Qualifiers
source                 1..17
                       mol_type = protein
                       organism = synthetic construct
SEQUENCE: 41
FEGVSEYYSY FSSVAGR                                                    17

SEQ ID NO: 42          moltype = AA  length = 18
FEATURE                Location/Qualifiers
source                 1..18
                       mol_type = protein
                       organism = synthetic construct
SEQUENCE: 42
FVYTSSYYST TFVAGEER                                                   18

SEQ ID NO: 43          moltype = AA  length = 19
FEATURE                Location/Qualifiers
source                 1..19
                       mol_type = protein
```

-continued

```
                          organism = unidentified
SEQUENCE: 43
FSVTLFYYSE LAFEVFFYR                                                19

SEQ ID NO: 44            moltype = AA  length = 20
FEATURE                  Location/Qualifiers
source                   1..20
                         mol_type = protein
                         organism = synthetic construct
SEQUENCE: 44
FATVESYYSV GAFVEASSTR                                               20

SEQ ID NO: 45            moltype = AA  length = 21
FEATURE                  Location/Qualifiers
source                   1..21
                         mol_type = protein
                         organism = synthetic construct
SEQUENCE: 45
FSAFYSYYSA EEEFSAYAVT R                                             21

SEQ ID NO: 46            moltype = AA  length = 17
FEATURE                  Location/Qualifiers
source                   1..17
                         mol_type = protein
                         organism = synthetic construct
SEQUENCE: 46
FAVVVGYYSS ETVYEAR                                                  17

SEQ ID NO: 47            moltype = AA  length = 18
FEATURE                  Location/Qualifiers
source                   1..18
                         mol_type = protein
                         organism = synthetic construct
SEQUENCE: 47
FTYAESYYSG STGATETR                                                 18

SEQ ID NO: 48            moltype = AA  length = 19
FEATURE                  Location/Qualifiers
source                   1..19
                         mol_type = protein
                         organism = synthetic construct
SEQUENCE: 48
FTSAVEYYSF EGSVYESGR                                                19

SEQ ID NO: 49            moltype = AA  length = 20
FEATURE                  Location/Qualifiers
source                   1..20
                         mol_type = protein
                         organism = synthetic construct
SEQUENCE: 49
FLEAAAYYLY VTFSVSAYVR                                               20

SEQ ID NO: 50            moltype = AA  length = 21
FEATURE                  Location/Qualifiers
source                   1..21
                         mol_type = protein
                         organism = synthetic construct
SEQUENCE: 50
FYGTAEYYGT EEFESGTYYE R                                             21
```

SEQUENCING DATA-ENCODED PEPTIDES FROM TANDEM MASS SPECTRA

CROSS-REFERENCE TO RELATED APPLICATIONS

This application claims priority to, and the benefit of, U.S. Provisional Patent Application Ser. No. 63/362,757 filed Apr. 11, 2022, the disclosure of which is incorporated by reference herein in its entirety.

REFERENCE OF SEQUENCE LISTING

A sequence listing file with a file name "P24143US01_SequenceListing.xml" in ST.26 XML format having a file size of 44,818 bytes created on Apr. 9, 2026 is incorporated herein by reference in its entirety.

LIST OF ABBREVIATIONS

AAC amino acid combination
DAG directed acyclic graph
DNA deoxyribonucleic acid
MS/MS tandem mass spectrometry
m/z mass-to-charge
OFF offset frequency function
RS Reed-Solomon
TIC total ion chromatogram

TECHNICAL FIELD

The present disclosure generally relates to sequencing of data-encoded peptides. Particularly, the present disclosure relates to a method of sequencing a data-encoded peptide from an experimental spectrum obtained in analyzing the data-encoded peptide by mass spectrometry or MS/MS.

BACKGROUND

Data storage using peptides offer several advantages over using DNAs. Most notably, a higher storage density can be achieved by using peptides over using DNAs in that unnatural amino acids can also be used for forming the peptides such that an alphabet size for encoding digital data into amino acids is enlarged. Furthermore, data storage using the peptides enjoy a longer storage time than using DNAs due to the property that peptides are more durable than DNAs.

Peptide sequencing is an important element in decoding data stored in data-encoded peptides. Mass spectrometry, especially MS/MS, is particularly useful for peptide sequencing. U.S. Pat. No. 11,315,023 B2 discloses techniques of sequencing data-encoded peptides from experimental spectra obtained in mass spectrometry or MS/MS. It is desirable to have improved techniques of sequencing the data-encoded peptides in mass spectrometry or MS/MS.

SUMMARY

An aspect of the present disclosure is to provide a computer-implemented method for sequencing a data-encoded peptide from an experimental spectrum. Raw data of the experimental spectrum are data of a histogram of intensity versus mass/charge ratio as originally obtained in analyzing the data-encoded peptide by mass spectrometry.

The method comprises: preprocessing the raw data for removing uninterpretable peaks to yield preprocessed data; identifying, from a spectrum graph, a first set of one or more candidate sequences contending for a peptide sequence of the peptide, wherein the spectrum graph is formed according to the preprocessed data rather than the raw data for generating a fewer number of candidate sequences to thereby reduce a time cost in sequencing; processing the first candidate-sequence set to estimate the peptide sequence; after a set of one or more estimates of the peptide sequence is obtained, verifying whether an individual peptide-sequence estimate is invalid; and purging the set of one or more estimates of the peptide sequence to remove any peptide-sequence estimate found to be invalid.

Preferably, the preprocessing of the raw data to yield the preprocessed data comprises: dividing a set of mass/charge ratios of the raw data into a plurality of subsets such that an individual subset consists of mass/charge ratios of isotopes of a fragment of the data-encoded peptide, an individual mass/charge ratio having a signal peak in the experimental spectrum, the isotopes of the fragment having a same charge of positive integer value; computing a monoisotopic mass of the fragment for the individual subset; computing an intensity of the fragment according to the raw data and the mass/charge ratios in the individual subset; and generating the preprocessed data. The preprocessed data includes a plurality of masses and a plurality of intensities, wherein the plurality of masses is formed with the monoisotopic mass of the fragment for the individual subset, and wherein an individual mass in the plurality of masses is associated with a corresponding intensity in the plurality of intensities.

Preferably, the preprocessed data further includes a first mass set of putative b-ions and a second mass set of putative y-ions for the experimental spectrum. The first and second mass sets are generated by distributing respective masses in the plurality of masses into the first and second mass sets.

Preferably, the identifying of the first candidate-sequence set from the spectrum graph further comprises the following steps. If a parent ion peak identified in the experimental spectrum has a charge of value 2, an individual candidate sequence in the first candidate-sequence set is identified via searching over the second mass set. If the charge of the parent ion peak is of value 3, the individual candidate sequence in the first candidate-sequence set is identified via searching over the first and second mass sets.

In certain embodiments, the processing of the first candidate-sequence set to estimate the peptide sequence comprises the following steps. If the first candidate-sequence set consists of a single candidate sequence, then assign the single candidate sequence in the first candidate-sequence set as one estimate of the peptide sequence, or else select one or more candidate sequences from the first candidate-sequence set to form a second set of one or more candidate sequences such that the one or more candidate sequences in the second candidate-sequence set are more probable to be the peptide sequence than non-selected candidate sequences in the first candidate-sequence set. If the second candidate-sequence set consists of a single candidate sequence, then assign the single candidate sequence in the second candidate-sequence set as one estimate of the peptide sequence. If the second candidate-sequence set consists of plural candidate sequences that are free from any AAC, then assign the plural candidate sequences in the second candidate-sequence set as estimates of the peptide sequence. If the second candidate-sequence set consists of plural candidate sequences that include one or more AACs, then use the raw data to determine valid amino-acid sequences for the one or more AACs. After the valid amino-acid sequences are determined, refine the candidate sequences in the second candidate-sequence set to generate a third set of one or more candidate sequences. The third candidate-sequence set is obtained from the second candidate-sequence set by using the determined valid amino-acid sequences to substitute the one or more AACs and then discarding any candidate sequence with an undetermined AAC. If the third candidate-sequence set consists of a single candidate sequence, then assign the single candidate sequence in the third candidate-sequence set as one estimate of the peptide sequence, or else select one or more candidate sequences from the third candidate-sequence set to form a fourth set of one or more candidate sequences such that the one or more candidate sequences in the fourth candidate-sequence set are more probable to be the peptide sequence than non-selected candidate sequences in the third candidate-sequence set. If the fourth candidate-sequence set consists of a single candidate sequence, then assign the single candidate sequence in the fourth candidate-sequence set as one estimate of the peptide sequence, or else assign plural candidate sequences in the fourth candidate-sequence set as estimates of the peptide sequence.

In certain embodiments, the selecting of the one or more candidate sequences from the first candidate-sequence set to form the second candidate-sequence set comprises the following steps. Select one or more candidate sequences with a longest length of consecutive amino acids among the candidate sequences in the first candidate-sequence set to form a fifth candidate-sequence set. If the fifth candidate-sequence set consists of a single candidate sequence, then assign the fifth candidate-sequence set to be the second candidate-sequence set, or else select one or more candidate sequences with a largest number of amino acids among plural candidate sequences in the fifth candidate-sequence set to form a sixth candidate-sequence set. If the sixth candidate-sequence set consists of a single candidate sequence, then assign the sixth candidate-sequence set to be the second candidate-sequence set, or else select one or more candidate sequences with a smallest match error among plural candidate sequences in the sixth candidate-sequence set to form a seventh candidate-sequence set. If the seventh candidate-sequence set consists of a single candidate sequence, then assign the seventh candidate-sequence set to be the second candidate-sequence set, or else select one or more candidate sequences with a highest average intensity value of retrieved amino acids among plural candidate sequences in the seventh candidate-sequence set to form an eighth candidate-sequence set. If the eighth candidate-sequence set consists of a single candidate sequence, then assign the eighth candidate-sequence set to be the second candidate-sequence set, or else select one or more candidate sequences with a highest number of occurrences for different ion types with different offsets among plural candidate sequences in the eighth candidate-sequence set to form the second candidate-sequence set.

In certain embodiments, the selecting of one or more candidate sequences from the third candidate-sequence set to form the fourth candidate-sequence comprises: selecting, from the third candidate-sequence set, one or more candidate sequences with a largest number of amino acids among the determined valid amino-acid sequences to form a ninth candidate-sequence set; and if the ninth candidate-sequence set consists of a single candidate sequence, then assigning the ninth candidate-sequence set to be the fourth candidate-sequence set, else selecting, from the ninth candidate-sequence set, one or more candidate sequences with a smallest match error among the determined valid amino-acid sequences to form the fourth candidate-sequence set.

In certain embodiments, the identifying of the first candidate-sequence set from the spectrum graph comprises:

identifying one or more paths that are valid and that have a longest length in the spectrum graph, wherein a valid path begins at a head vertex, and ends at a tail vertex with a mass of the data-encoded peptide; using each of the identified one or more paths to generate a new candidate sequence; and allocating the new candidate sequence to the first candidate-sequence set.

In certain embodiments, the identifying of the first candidate-sequence set from the spectrum graph comprises the steps of: (a) sorting the plurality of masses in a descending order of corresponding intensities of respective masses to thereby form an ordered sequence of masses, wherein the ordered sequence of masses ranks the plurality of masses with a highest-ranking mass being associated with a highest corresponding intensity; (b) given a selected mass and a selected number of higher-ranking masses in the ordered sequence of masses, identifying one or more highest-intensity-based tags in the spectrum graph, wherein an individual highest-intensity-based tag is a partial sequence consisting of a first amino acid having the selected mass and a plurality of remaining amino acids each having a mass selected from the selected number of higher-ranking masses; (c) processing the one or more highest-intensity-based tags, wherein processing the individual highest-intensity-based tag comprises: determining a prefix and a suffix for the individual highest-intensity-based tag; if the prefix and suffix are successfully determined, then combining the prefix, the individual highest-intensity-based tag and the suffix to form a new candidate sequence; and allocating the new candidate sequence to the first candidate-sequence set; (d) sequentially using successive values in a strictly decreasing sequence of values as the selected number of higher-ranking masses to repeat the steps (b) and (c) until the first candidate-sequence set is not empty or the strictly decreasing sequence is exhausted; and (e) starting from the highest-ranking mass, sequentially using successive masses in the ordered sequence of masses as the selected mass to repeat the steps (b)-(d) until the first candidate-sequence set is not empty or a preselected number of higher-ranking masses in the ordered sequence of masses is reached.

In certain embodiments, the determining of the prefix and suffix for the individual highest-intensity-based tag comprises the following steps. Identify the prefix as a first path that is valid and that has a longest length in the spectrum graph, wherein: the first path connects a head amino acid and a head of the individual highest-intensity-based tag; one or more first AACs with a total length at most a first maximum length are allowable to be present in the identified first path; if the charge of the parent ion peak is of value 2, then the first maximum length is set as $L_{p1}$; and if the charge of the parent ion peak is of value 3, then the first maximum length is initially set as $L_{p1}$ in finding the first path, and is relaxed to $L_{p2}$ in response to failure of finding the first path under the first maximum length being $L_{p1}$, where $L_{p2}>L_{p1}$. Identify the suffix as a second path that is valid and that has a longest length in the spectrum graph, wherein: the second path connects a tail of the individual highest-intensity-based tag and a tail amino acid; one or more second AACs with a total length at most a second maximum length are allowable to be present in the identified second path; if the charge of the parent ion peak is of value 2, then the second maximum length is set as $L_{s1}$; and if the charge of the parent ion peak is of value 3, then the second maximum length is initially set as $L_{s1}$ in finding the second path, and is relaxed to $L_{s2}$ in response to failure of finding the second path under the second maximum length being $L_{s1}$, where $L_{s2}>L_{s1}$.

In certain embodiments, whether the individual peptide-sequence estimate is invalid may be determined by: checking a length of the individual peptide-sequence estimate against a predetermined correct length of the peptide sequence; performing order checking for amino acids "G" and "L" in the individual peptide-sequence estimate; performing order checking based on order-checking bits carried in the data-encoded peptide; or any combination thereof.

Other aspects of the present disclosure are disclosed as illustrated by the embodiments hereinafter.

BRIEF DESCRIPTION OF THE DRAWINGS

FIG. 1 depicts a 4095×17 block of 3-bit symbols having a total number of 208845 (=4095×17×3) bits as a first example of designing data carried on data-encoded peptides.

FIG. 11 depicts a flowchart for illustrating a computer-implemented method for sequencing a data-encoded peptide from an experimental spectrum in accordance with an exemplary embodiment of the present disclosure.

Figure 2:
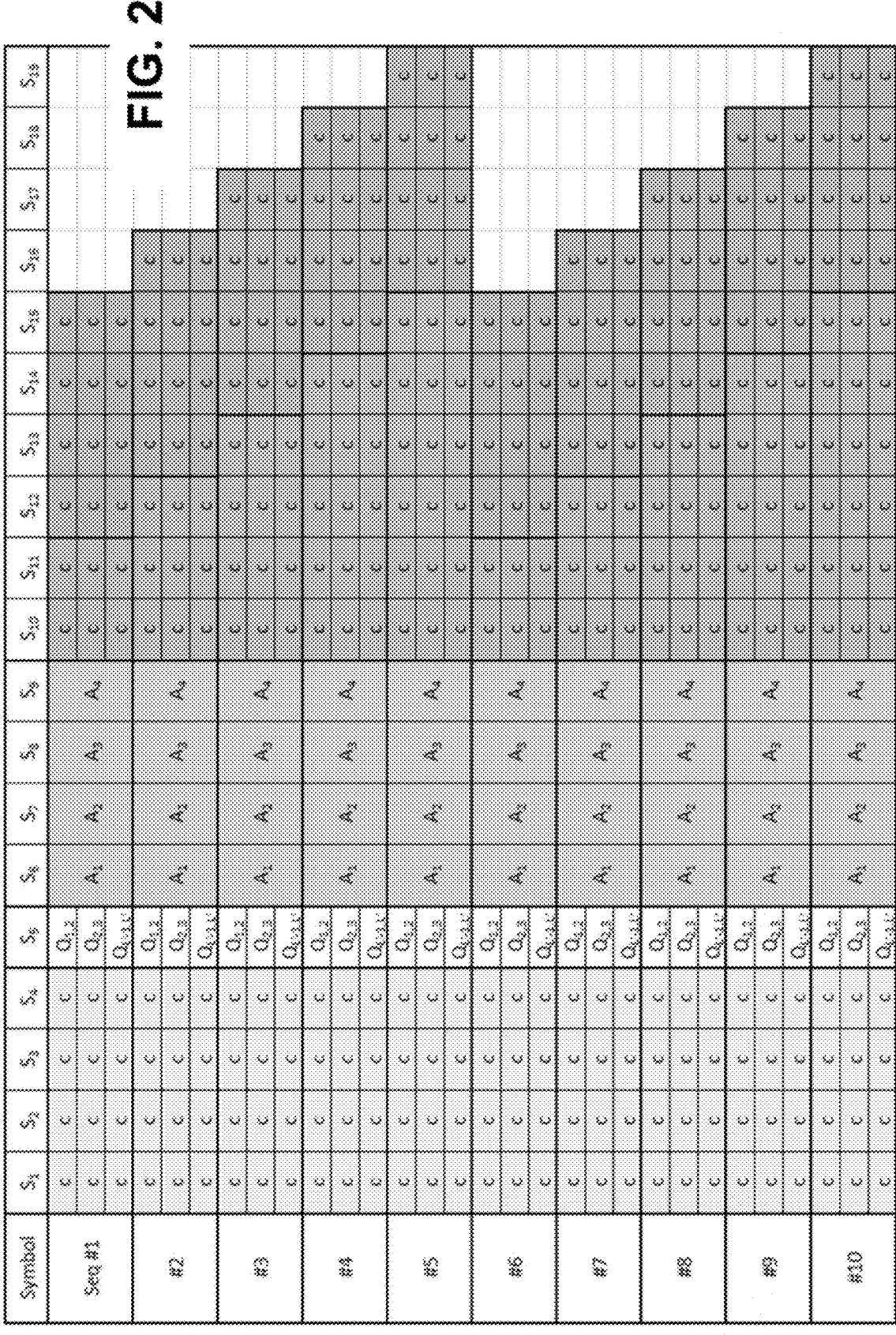
FIG. 2 depicts a 4095×19 block of 3-bit symbols having a total number of 98268 information bits, 12285 order-checking bits and 3 RS codes as a second example of designing data carried on data-encoded peptides.
Figure 2:
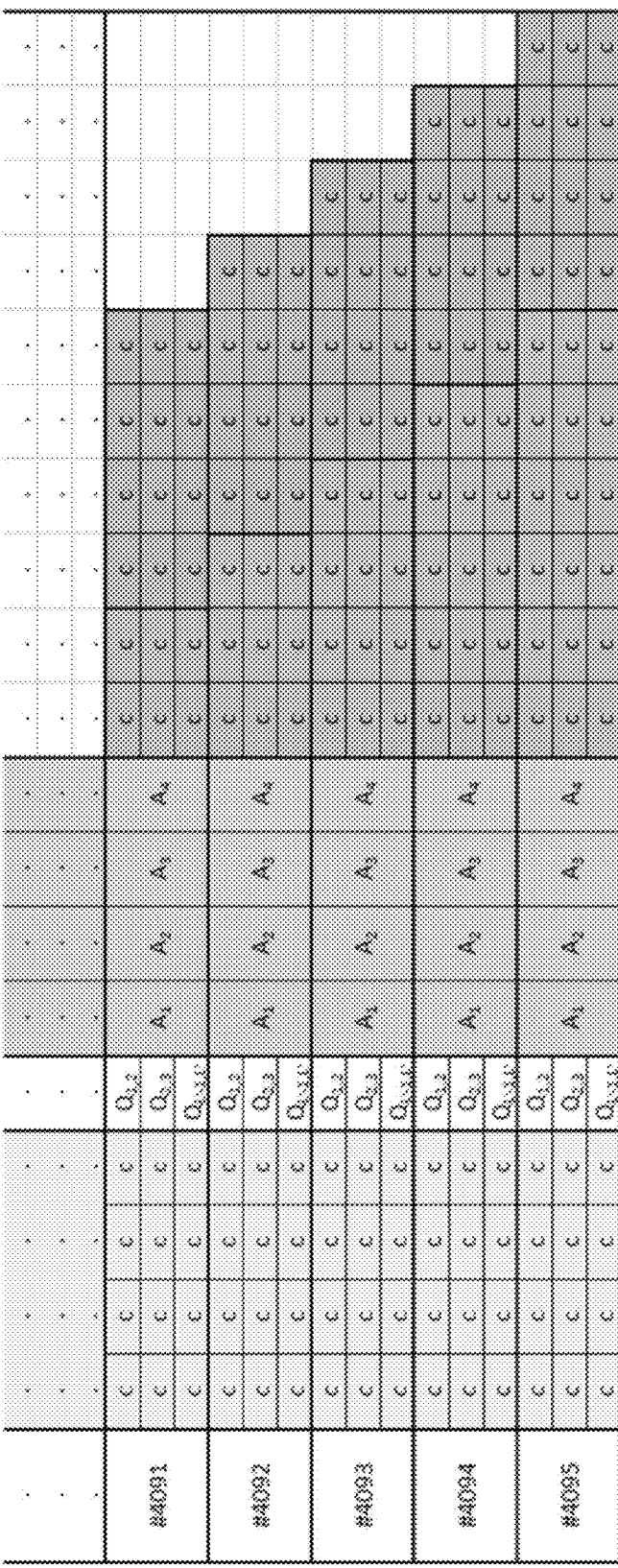

Skilled artisans will appreciate that elements in the figures are illustrated for simplicity and clarity and have not necessarily been depicted to scale. For example, the dimensions of some of the elements in the illustrations, block diagrams or flowcharts may be exaggerated in respect to other elements to help to improve understanding of the present embodiments.

DETAILED DESCRIPTION

The present disclosure is concerned with peptide sequencing for data-encoded peptides. Two related peptide sequencing methods are disclosed, namely, a two-stage sequencing method and a highest-intensity-tag based sequencing method.

Section A describes the technical terms and notations used in the present disclosure. Section B provides some examples of designing peptide sequences for data-encoded peptides. The resultant peptide sequence designs are occasionally referenced in explaining the two sequencing methods. The problem of sequencing data-encoded peptides is modelled in Section C. The two-stage sequencing method and the highest-intensity-tag based sequencing method are elaborated in Sections D and E, respectively. Section F provides a checking method based on the design of peptide sequences for verifying candidate sequences during generation of these sequences. Embodiments of the present disclosure are developed mainly based on the developments in Sections D-F.

A. Technical Terms and Notations

The following terms and notations are used herein in the specification and appended claims.

"A peptide" is a physical chain of amino acids linked by peptide bonds.

"A data-encoded peptide" is a peptide whose constituent amino acids are purposely selected and positioned in the peptide in a meaningful manner for representing digital data.

"A peptide sequence" of a peptide is a digital string representing an ordered sequence of amino acid residues in the peptide. Thus, the ordered sequence specifies an order of assembly of constituent amino acids in forming the peptide.

"A head amino acid" is defined as an amino acid residue next to the N-terminus of a peptide. That is, the head amino acid is an N-terminal amino acid residue of the peptide.

"A tail amino acid" is defined as an amino acid residue next to the C-terminus of a peptide. That is, the tail amino acid is a C-terminal amino acid residue of the peptide.

The meanings of "b-ion", "y-ion" and other fragment ions due to cleaving peptide bonds of a peptide are commonly understood by those skilled in the art. It is intended that the present disclosure adopts commonly-accepted interpretation of b-ion, y-ion and other fragment ions obtained by breaking up peptide bonds of a peptide. A b-ion of a peptide is a charged fragment of the peptide after the peptide is split at a peptide bond between two constituent amino acids, where the b-ion contains the N-terminus of the peptide. A y-ion of a peptide is a charged fragment of the peptide after the peptide is split at a peptide bond between two constituent amino acids, where the y-ion contains the C-terminus of the peptide.

"A tag" is a partial sequence of an amino-acid sequence where the partial sequence is formed by consecutive amino acids.

"An AAC" is an order-independent composition of amino acids. Note that an order of assembly of constituent amino acids in an AAC needs not be known in modeling or initially establishing the AAC. Nonetheless, in peptide sequencing, it is often necessary to resolve the order of assembly for the AAC based on additional information on the AAC.

"A mass spectrum" is a histogram of intensity versus mass/charge ratio in a chemical sample analyzed by a mass spectrometer.

"An experimental spectrum" is a mass spectrum obtained in an experiment.

"Raw data of an experimental spectrum," are data of a histogram of intensity versus mass/charge ratio as originally obtained in analyzing a chemical sample by mass spectrometry. In practice, the originally obtained histogram is usually obtained from a mass spectrometer. In the present disclosure, however, it is intended that signal enhancement techniques (such as noise reduction algorithms) may be used in preparing the originally obtained histogram from physical measurement data obtained from the mass spectrometer.

"A match error" is defined as a mean error between observed mass values for amino acids retrieved from an experimental spectrum and actual mass values of the amino acids normalized by the corresponding observed mass values.

"A parent ion peak", also known as a molecular ion peak, in a mass spectrum is a peak that stems from a molecule that is electrically charged when the molecule is analyzed in a mass spectrometer without any fragmentations.

Denote $A=\{a_1, a_2, \ldots, a_k\}$ as a set of amino acids that are selectable to be used as a constituent amino acid in forming a data-encoded peptide, where K is the number of different amino acids in the set, and $a_i$, $i \in \{1, \ldots, K\}$, is an ith amino acid in A. In other words, A is an alphabet of amino acids for forming the data-encoded peptide.

Denote $g=\{g_1, g_2 \ldots, g_K\}$ as a mass set of amino acid residues that are selectable to be used in forming the data-encoded peptide, where $g_i$, $i \in \{1, \ldots, K\}$ is the mass of an amino acid residue corresponding to $a_i$.

Denote $P=\{P_1, P_2, \ldots, P_N\}$ as a peptide sequence of a peptide, where N is the number of constituent amino acids that collectively form the peptide, and $P_i$, $i \in \{1, \ldots, N\}$, is an ith amino acid residue in the peptide sequence. Without causing confusion, the peptide is also denoted by P, and it is understood that the peptide referred to as P is a peptide whose peptide sequence is P.

Denote $m=\{m_1, m_2, \ldots, m_N\}$ as a mass set of amino acid residues in the peptide P, where $m_i$, $i \in \{1, \ldots, N\}$, is the mass of $P_i$.

Denote $m_H$ as the mass of a hydrogen atom or a proton.

Denote $m_{OH}$ as the mass of a hydroxyl group.

Denote $m_{Ngroup}$ as the mass of an N-terminal functional group attached to a head amino acid of the peptide P. If P has an unprotected N-terminus, the mass of the N-terminal functional group is equal to $m_H$.

Denote $m_{Cgroup}$ as the mass of a C-terminal functional group attached to a tail amino acid of the peptide P. If P has an unprotected C-terminus, the mass of the C-terminal functional group is equal to $m_{OH}$.

Denote $m_{head}$ and $m_{tail}$ as the masses of the head amino acid and of the tail amino acid, respectively. The masses $m_{head}$ and $m_{tail}$ can be zero if there are no fixed amino acids.

Denote M as the mass of the peptide P. Note that M is given $$M = m_{Ngroup} + m_{Cgroup} + \sum_{j=1}^{N} m_j.$$

Denote $m_b=\{m_{b,1}, m_{b,2}, \ldots, m_{b,N+1}, m_{b,N+2}\}$ as the mass set of b-ions in the peptide P, where $m_{b,i+1}=m_{b,i}+m_i$ for $i \in \{1, \ldots, N+1\}$ with $m_{b,1}=M_{Ngroup}-m_H$. Note that: $m_{b,2}=(m_{Ngroup}-m_H)+m_{head}$; $m_{b,N}=M-m_H-m_{Cgroup}-m_{tail}$; $m_{b,N+1}=M-m_H-m_{Cgroup}$, and $m_{b,N+2}=M$.

Denote $m_y=\{m_{y,1}, m_{y,2}, \ldots, m_{y,N+1}, m_{y,N+2}\}$ as the mass set of y-ions in the peptide P, where $m_{y,i+1}=m_{y,i}-m_i$ for $i \in \{1, \ldots, N+1\}$ with $m_{y,1}=M-(m_{Ngroup}-m_H)$. Note that $m_y=M-m_b$. Also note that: $m_{y,2}=M-(m_{Ngroup}-m_H)-m_{head}$; $m_{y,N}=m_H+m_{Cgroup}+m_{tail}$; $m_y,N+1=m_H+m_{Cgroup}$; and $m_y,N+2=0$.

Denote $\Delta=\{\Delta_1, \Delta_2 \ldots, \Delta_N\}$ as the mass difference set between a theoretical (mass) spectrum and an experimental (mass) spectrum, where $\Delta_i \in [-\delta, +\delta]$, $i \in \{1, \ldots, N\}$, and $\delta$ is a tolerance value.

Denote T(P) as the theoretical spectrum generated by the peptide P.

Denote S as a MS/MS spectrum obtained by tandem mass spectrometry.

Denote L as the number of pairs of m/z ratio and intensity representing the spectrum S.

Denote $z=\{z_1, z_1, \ldots, z_L\}$ as the set of charges for the spectrum S. Usually, $z_i$ is selected from 1, 2 and 3.

Denote $(m/z)=\{(m/z)_1, (m/z)_2, \ldots, (m/z)_L\}$ as a set of mass/charge ratios for the spectrum S.

Denote $\rho$ as the number of subsets in the spectrum S. In each subset, all (m/z) ratios are isotopes of a particular fragment, with a charge value equaling the inverse of difference between consecutive mass/charge ratios.

Denote $M_{out}$ as the mass output of a mass spectrometer corresponding to the highest intensity. The mass output $M_{out}$ may be a monoisotopic peak, or the peak that follows (with mass+1.007276 Da).

Denote $G_i$, $i \in \{1, 2, \ldots, \rho\}$, as an ith subset in the spectrum S.

Denote $m'_i$ as a monoisotopic mass for the subset $G_i$. Note that $m'_i$ can be calculated by $m'_i=(m/z)_{i,0}z'_{i,0}-m_H z'_{i,0}$, where $(m/z)_{i,0}$ is the lowest value in the subset $G_i$, and $z'_{i,0}$ is the corresponding charge for $(m/z)_{i,0}$.

Denote $m'_b=\{m'_{b,1}, m'_{b,2}, \ldots, m'_{b,L}\}$ as the mass set of putative b-ions for the spectrum S, where $m'_{b,i}=(m/z)_i z_i - m_H z_i$, $i=1, \ldots, L$.

Denote $m'_y=\{m'_{y,1}, m'_{y,2}, \ldots, m'_{y,L}\}$ as the equivalent b-ion mass set of putative y-ions for the spectrum S, where $m'_{y,i}=M-[(m/z)_i z_i-m_H z_i]$, $i=1, \ldots, L$.

Denote $I=\{I_1, I_2, \ldots, I_L\}$ as a set of intensities for the spectrum S, where the intensity $I_i$ corresponds to $(m/z)_i$ for each i, $i=1, 2, \ldots, L$.

Denote J as the ranking of the intensity.

Denote $m'_{B,J}$ as the mass of the putative b-ion with the Jth highest intensity for the spectrum S.

Denote $m'_{Y,J}$ as the equivalent b-ion mass of the putative y-ion with the Jth highest intensity for the spectrum S.

Denote $J_{max}$ as the maximum number of higher-ranking-intensity masses allowed to be a start point in finding a tag.

Denote n as the number of candidate sequences.

Denote W as the number of masses with higher ranking intensity used for a tag-finding scheme.

Denote V as the maximum number of iterations in a highest-intensity-tag based sequencing method.

Denote $L_{AAC}$ as the length of an AAC.

Denote $L_{p1}$ and $L_{p2}$ as two maximum lengths of AACs used for limiting a length of each AAC in a prefix.

Denote $L_{s1}$ and $L_{s2}$ as two maximum lengths of AACs used for limiting a length of each AAC in a suffix.

Denote $P_L$ as the position of the last amino acid "L" in peptide sequence P.

Denote $P_G$ as the position of the first amino acid "G" in the peptide sequence P.

Denote L' as the number of symbols in a row for a 4095×17 block or for a 4095×19 block. Note that L'=N−2.

Denote Seq as the index of a sequence in the block, where Seq ranges from 1 to 4095.

Denote $S_1, S_2, \ldots, S_{L'}$ be L' symbols taken from the block and encoded in the peptide P (excluding the head and tail amino acids).

Denote $Q_{i,j}$ as an order-checking bit used to protect the order of symbols $S_i$ and $S_j$, where $(i, j)$ is selected from $(1,2)$, $(2,3)$ and $(L'-1, L')$. For details of order-checking bits, see U.S. Pat. No. 11,315,023 B2.

Denote $A_1$, $A_2$, $A_3$ and $A_4$ as the address symbols $S_6$, $S_7$, $S_8$ and $S_9$, respectively.

Denote $n_i$ as the code length of an ith RS code.

Denote $k_i$ as the number of 12-bit information symbols for the ith RS code.

Denote R as an overall code rate.

One-letter symbols are occasionally used to represent different amino acids in, e.g., describing a peptide's structure. Amino acids and their respective one-letter symbols (enclosed in paratheses) are listed as follows: Alanine (A); Arginine (R); Asparagine (N); Aspartate (D); Cysteine (C); Glutamine (Q); Glutamate (E); Glycine (G); Histidine (H); Isoleucine (I); Leucine (L); Lysine (K); Methionine (M); Phenylalanine (F); Proline (P); Serine(S); Threonine (T); Tryptophan (W); Tyrosine (Y); Valine (V); Selenocysteine (U); and Pyrrolysine (O).

B. Design of Data-Encoded Peptides

In the design of the fixed-length sequences, each peptide sequence has L' (L'=17) 3-bit symbols, which are denoted as $S_1$, $S_2$, . . . , $S_{17}$. We make the assumptions that: (i) 15%, 10% and 25%, respectively, of the 4-symbol sequences $\{S_1, S_2, S_3, S_4\}$, $\{S_{10}, S_{11}, S_{12}, S_{13}\}$ and $\{S_{14}, S_{15}, S_{16}, S_{17}\}$ cannot be recovered correctly for the length-17 symbol sequence $\{S_1, S_2, . . . , S_{17}\}$; and (ii) there are three ambiguous orders of symbols, which are the order of $S_1$ and $S_2$, the order of $S_2$ and $S_3$, and the order of $S_{16}$ and $S_{17}$.

Then, we propose an error-correction method based on the RS code. The method uses: (i) three RS codes to recover the original data even when any arbitrary 15% of 4-symbol sequences $\{S_1 S_2 S_3 S_4\}$, any arbitrary 10% of 4-symbol sequences $\{S_{10} S_{11} S_{12} S_{13}\}$, and any arbitrary 25% of 4-symbol sequences $\{S_{14} S_{15} S_{16} S_{17}\}$, cannot be recovered correctly, and (ii) three order-checking bits for the order of $S_1$ and $S_2$, the order of $S_2$ and $S_3$ and the order of $S_{16}$ and $S_{17}$ in each peptide sequence, respectively.

As shown in FIG. 1, a 4095×17 block of 3-bit symbols is first constructed which has a total of 208845 (=4095×17×3) bits. In each row of the block, there are 17 symbols (i.e. $S_1$, $S_2$, . . . , $S_{17}$) to represent a 17-mer data-encoded peptide. Four of the symbols, namely $S_6$, $S_7$, $S_8$ and $S_9$, are defined by $A_1$, $A_2$, $A_3$ and $A_4$, respectively. They serve as the address of the peptide sequence and assume one of the following values: 0000 (in octal form), 0001, 0002, . . . , 0007, 0010, . . . , 0777, 1000, . . . , 7775, 7776. The three order-checking bits carried in $S_5$ are denoted as $Q_{1,2}$, $Q_{2,3}$ and $Q_{16,17}$, which are used to denote the order of $S_1$ and $S_2$, the order of $S_2$ and $S_3$ and the order of $S_{16}$ and $S_{17}$, respectively. The order-checking bit $Q_{i,j}$ is "1" if the value of $S_i$ is larger than that of $S_j$; otherwise, the order-checking bit is "0". The remaining 12 symbols of each row, i.e. $S_1$, $S_2$, . . . , $S_5$, $S_{10}$, . . . , $S_{17}$, can then be used to restore the coded bits c, including the information bits and parity bits of the error-correction codes.

Next, we assume that 15%, 10% and 25%, respectively, of the 4-symbol sequences $\{S_1 S_2 S_3 S_4\}$, $\{S_{10} S_{11} S_{12} S_{13}\}$ and $\{S_{14} S_{15} S_{16} S_{17}\}$ cannot be recovered correctly. We then use three different $(n_i, k_i)$ RS codes for these three partial sequences, where $n_i$ is the code length of the ith RS code and $k_i$ is the number of 12-bit information symbols for the ith RS code. It is assumed that $n_i$ takes the same value 4095 for i=1, 2 and 3, i.e. $n_1=n_2=n_3=4095$, while $k_1=2867$, $k_2=3275$ and $k_3=2047$ for the 1st, 2nd and 3rd RS codes, respectively. The resultant (4095, 2867) RS code (denoted as RS1), (4095, 3275) RS code (denoted as RS2) and (4095, 2047) RS code (denoted as RS3) can correct up to 614, 410 and 1024 12-bit symbol errors, respectively. For the whole block, there are at most $(k_1+k_2+k_3)\times 12=98268$ bits that can be used as the data bits, and the maximum overall code rate R of the block is given by 98268/(4095×17×3)=0.4705.

For our dataset A, the number of information bits is 96224 in which there are 47965 bits of "0" and 48259 bits of "1". Since each 4095×17 block can contain up to 98268 information bits, we fill the remaining 98268−96224=2044 bit positions in each block with "0" and "1" with equal probability. Then these 98268 bits are divided into three parts. The first part is used to fill the symbols $\{S_1 S_2 S_3 S_4\}$ in the row sequences ranging from $(n_1-k_1+1)$ to $n_1$, the second part to fill the symbols $\{S_{10} S_{11} S_{12} S_{13}\}$ in the row sequences ranging from $(n_2-k_2+1)$ to $n_2$, and the third part to fill the symbols $\{S_{14} S_{15} S_{16} S_{17}\}$ in the row sequences ranging from $(n_3-k_3+1)$ to $n_3$. In the encoding process, RS1 uses the bits in the first part to generate the coded symbols to fill $\{S_1 S_2 S_3 S_4\}$ in the row sequences ranging from 1 to $(n_1-k_1)$; RS2 uses the bits in the second part to generate the coded symbols to fill $\{S_{10} S_{11} S_{12} S_{13}\}$ in the row sequences ranging from 1 to $(n_2-k_2)$; RS3 uses the bits in the third part to generate the coded symbols to fill $\{S_{14} S_{15} S_{16} S_{17}\}$ in the row sequences ranging from 1 to $(n_3-k_3)$.

Finally, we count the number of 3-bit symbols equating 000, 001, . . . , 111, (or denoted by 0 to 7) in the block. The numbers for symbols 000, 001, . . . , 111, are 8294, 8380, 8927, 9181, 8831, 8754, 8671 and 8577, respectively. The actual code rate R for our dataset A is then given by 96224/(4095×17×3)=0.4607.

Now, we consider the case that the lengths of the sequences vary and we assume one of the following values: 15, 16, 17, 18, and 19. Then we construct the 4095×19 block shown in FIG. 2. We regard every 5 sequences with lengths 15, 16, 17, 18, and 19 as a group. The length $L'_j$ for the jth sequence in each group can be evaluated by $L'_j=15+$mod (Seq−1,5), where mod represents the modulo operation, and Seq is the index of the sequence in the block and ranges from 1 to 4095. Since Seq and the address sequence $\{A_1 A_2 A_3 A_4\}$ are one-to-one mapping with Seq=$A_1 \times 8^3 + A_2 \times 8^2 + A_3 \times 8^1 + A_4 + 1$, a length checking based on the address can be used to determine the correctness of the sequence.

Let $$S_i^{(j)}$$

be the ith symbol of the jth sequence in each group. As can be observed in FIG. 1, we can transform the 4095×17 block to the 4095×19 block by: (i) moving $$S_{10}^{(1)} \text{ and } S_{11}^{(1)}$$

of Sequence 1 and inserting them before $$S_{10}^{(5)}$$

of Sequence 5; and moving $$S_{10}^{(2)}$$

of Sequence 2 and inserting it before $$S_{10}^{(4)}$$

of Sequence 4.

Since the variable-length sequences shown in FIG. 2 are constructed by moving the symbols in the fixed-length sequences shown in FIG. 1, the overall code rate R of the 4095×19 block in FIG. 2 is the same as that of the 4095×17 block in FIG. 1.

Next, we map the 3-bit symbols (symbols from "0" to "7" corresponding to the three bits from 000 to 111) in the 4095×17 block into 8 amino acids (Y, T, E, A, S, V, G and F), and obtain the 4095 sequences with "G" corresponding to Symbol "6".

Moreover, if mass conflict occurs, that is, the mass M of a sequence is within the tolerance range (25 ppm) of other sequences, then the amino acid "G" is replaced by an unused amino acid "L". This process starts from the first "G" near the head amino acid. After the replacement of only one "G", if the updated mass M still falls in the tolerance range of other sequences, the replacement process continues by shifting to the next "G" of the original sequence. After this process is performed, the sequences consist of 9 possible amino acids with both "G" and "L" corresponding to Symbol "6". Since all amino acids of "L" should be presented before "G", the order of "G" and "L" can be used to distinguish the validation of an estimated peptide sequence after peptide sequencing. The effect of this replacement can be seen from an example dataset with 4095 data-encoded peptides, with fixed N-terminal amino acid H and fixed C-terminal amino acid R, and with the amino acids in between encoded using the mapping of the 3-bit symbols into the 8 amino acids as described above. Before replacement, the number of data-encoded peptides with mass conflict was 3630, and there were 732 groups of data-encoded peptides where all data-encoded peptides in each group have the same M within the tolerance range. After replacement, the number of data-encoded peptides with mass conflict was dropped to 2746, and there were 619 groups of data-encoded peptides where all data-encoded peptides in each group have the same M within the tolerance range. It reduces the problem where two or more isobaric peptides co-elute, thus reducing the number of overlapping MS/MS spectra that interfere sequencing.

C. Peptide Sequencing Problem

Generally, under the conditions of using the whole set of 20 natural amino acids and the existing peptides with natural amino acids, most of the existing sequencing algorithms, including Sherenga, PepNovo, NSNovo, pNovo, uniNovo, NovoHCD and Novor, rely on training by the properties of the data. For example, the OFFs introduced by V. DANČÍK et al. ("De Novo Peptide Sequencing via Tandem Mass Spectrometry, *Journal of Computational Biology*, vol. 6, no. 3/4, 1999, pp. 327-342") are first empirically derived by counting the occurrence frequencies of different ion types and feature types in the training data. After candidate paths are obtained by using the DAG model and the dynamic programming for Sherenga, pNovo and uniNovo, the OFFs are used as reference for the scoring of these paths.

In peptide-based data storage, the amino acids are generated by any combinations of bits "0" and "1" and hence the peptide sequences are completely random. Therefore, no suitable training sequences are available for existing sequencing algorithms. Also, peptide-based data storage may use some or all of the natural amino acids depending on the design of peptides. In addition, unnatural amino acids can be used.

A constraint for the dynamic algorithm is that no training spectra are provided for the sequencing of the digital data bearing peptides. Accordingly, de novo sequencing based on the graph model is utilized for determining peptide sequences. In the graph model, the MS/MS spectrum is represented by a DAG, called a spectrum graph. The peaks of the spectrum can be taken as vertices, while an edge is added between two vertices when the mass gap between two peaks is equal to the mass of an amino acid. The objective of dynamic programming is to find the longest path (or the best path) in the graph starting from the head vertex to the tail vertex. An alternative approach to identify the sequence is to start with the middle part of the MS/MS spectrum. For example, the sequence tagging method first infers a partial sequence called as a tag, and then finds the whole sequence that can match the tag. In the tag-based method, tags are first found from the MS/MS spectrum based on some scoring schemes. The inference of the sequence then relies on peptide comparison using the database search method or on extending the valid path of the tag in the middle position of the path using the de novo sequencing.

The peptide sequencing problem is outlined in Table 1, with knowledge of information of the amino acids used, the spectrum S, the mass of the whole sequence, and the head and tail amino acids. The sequencing problem is to find the peptide P, whose theoretical spectrum T(P) best matches the experimental spectrum S. In many practical situations, the length N of the peptide sequence is fixed and known. Thus, candidate peptides of length not equal to N are discarded. Two sequencing methods, namely a two-stage sequencing method and a highest-intensity-tag based sequencing method, are disclosed herein. For both methods, the sequences are estimated by first inferring a partial sequence with a small amount of reliable information and then finding the missing part of the sequence with less reliable data or the raw data. This approach gives an advantage of improving the speed of sequencing by generating a fewer number of candidates. Moreover, due to the introduction of the tag, the highest-intensity-tag based sequencing method is more effective in rejecting unlikely candidates.

TABLE 1

| Description of the peptide sequencing problem. | |
| --- | --- |
| Input: | Set A of amino acids. |
| | Mass set g for the amino acids in set A. |
| | Experimental spectrum S. |
| | Set (m /z) of mass/charge ratios of the spectrum S. |
| | Set I of intensity of spectrum S. |
| | Length N of the peptide sequence. |
| | Head and tail amino acids used for the peptide. |
| | Mass M of the whole sequence. |
| Output: | Peptide sequence P of length N. |
| Problem: | Estimate a peptide P that most likely generates the experimental spectrum S. |

D. Peptide Sequencing: Two-Stage Sequencing Method

Figure 3:
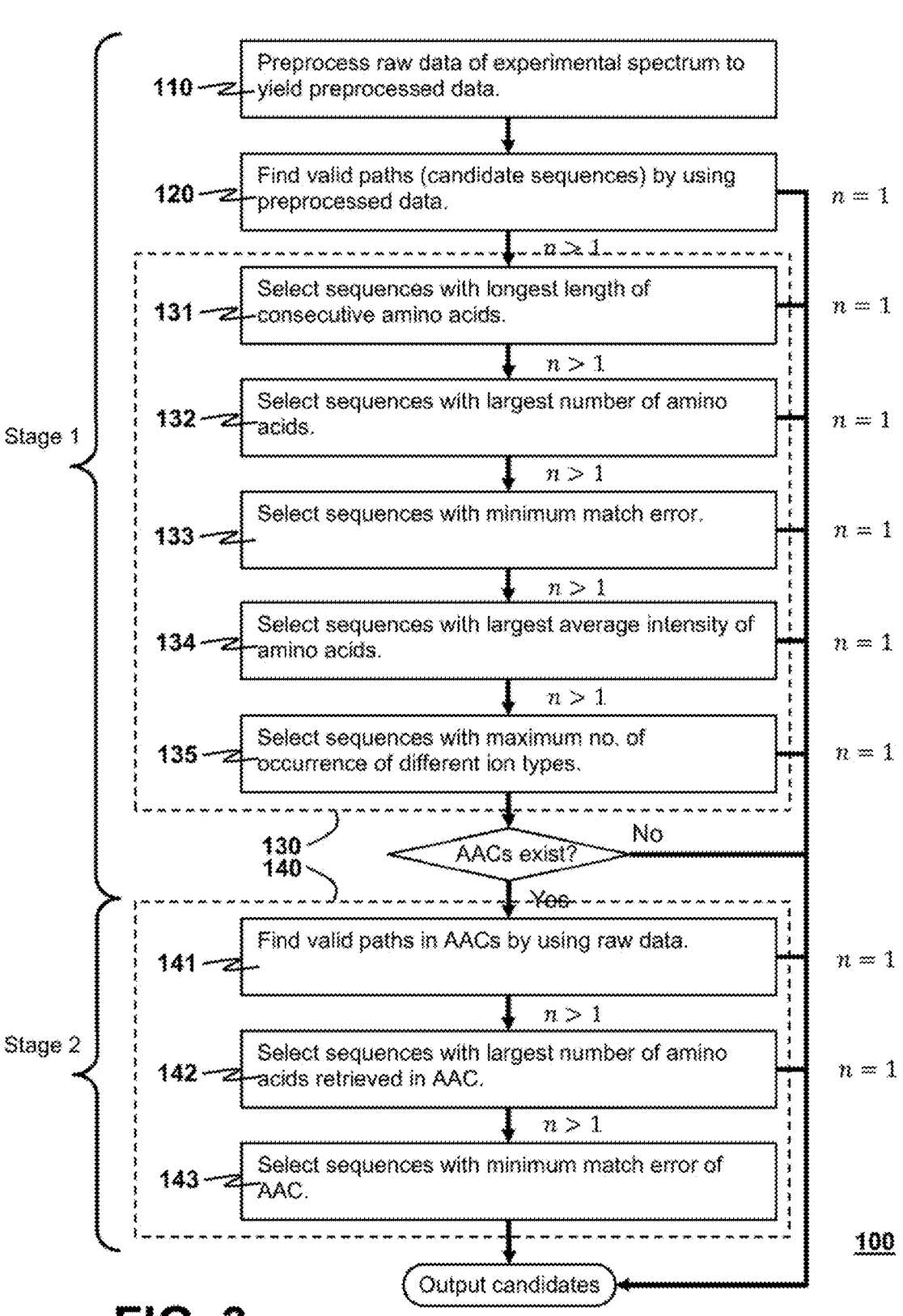
FIG. 3 depicts a flowchart illustrating a method of two-stage sequencing in accordance with certain embodiments of the present disclosure.

FIG. 3 shows a flowchart of exemplary steps for illustrating a method 100 of two-stage sequencing. Four steps are involved in the two-stage sequencing method 100: preprocessing, candidate sequence generation, sequence selection, and candidate refining. As shown in FIG. 3, steps 110, 120 and 130 belong to the first stage, i.e. Stage 1, while step 140 is processed in the second stage, i.e. Stage 2. In Stage 1 of the two-stage sequencing method 100, a partial sequence is inferred by using the preprocessed data after the step 110 is performed. In Stage 2, the remaining part of the sequence is determined based on the raw data.

In the step 110, preprocessing is performed. The goal of the preprocessing is twofold. First, it is to remove some uninterpretable peaks caused by noise and uncertainty. Second, it is to convert the mass/charge ratio set (m/z) to the corresponding mass sets $m'_b$ and $m'_y$. Given a set of mass/charge (m/z) ratios at which signal peaks are present in the experimental spectrum S, these ratios are divided into $\rho$ subsets $G_1$, $G_2$, . . . , $G_p$, where in each subset $G_i$, $i \in$ {1, 2, . . . , $\rho$}, all (m/z) ratios are isotopes of a particular fragment having the same chemical composition. Furthermore, the isotopes in each subset have the same charge state, which is represented by a charge of positive integer value (usually 1, 2 or 3). For each subset $G_i$, a monoisotopic mass $m'_i$ is calculated by $m'_i = (m/z)_{i,0} z'_{i,0} - m_H z'_{i,0}$, i=1, 2, . . . , $\rho$, where $(m/z)_{i,0}$ is the lowest value in this subset, and $z'_{i,0}$ is the corresponding charge for $(m/z)_{i,0}$. These $m'_i$ values are then distributed between the mass sets $m'_b$ and $m'_y$. In certain embodiments, one of the criteria of distribution is based on the intensities corresponding to the $m'_i$ values. In certain embodiments, one of the criteria of distribution is the isotopic pattern of the (m/z) ratios in $G_i$. In certain embodiments, one of the criteria of distribution is based on the fact if $$m'_i \text{ is in } m'_{b,i},$$

then there is a corresponding $$m'_j \text{ in } m'_{y,j}, \text{ where } m'_j = M - m'_i.$$

In certain embodiments, the distribution is determined real-time in step 120 to be described later. In certain embodiments, only those data with typical property of charges are reserved as the preprocessed data such that the preprocessed data may be more reliable than the raw data. However, in the event of the incomplete or ambiguous data (e.g., data lacking charge property), some useful mass values may be discarded in the preprocessing based on the abovementioned criteria. Hence, in the case when missing/uncertain elements of the sequence exist in Stage 1, the raw data may be considered in Stage 2.

Figure 4:
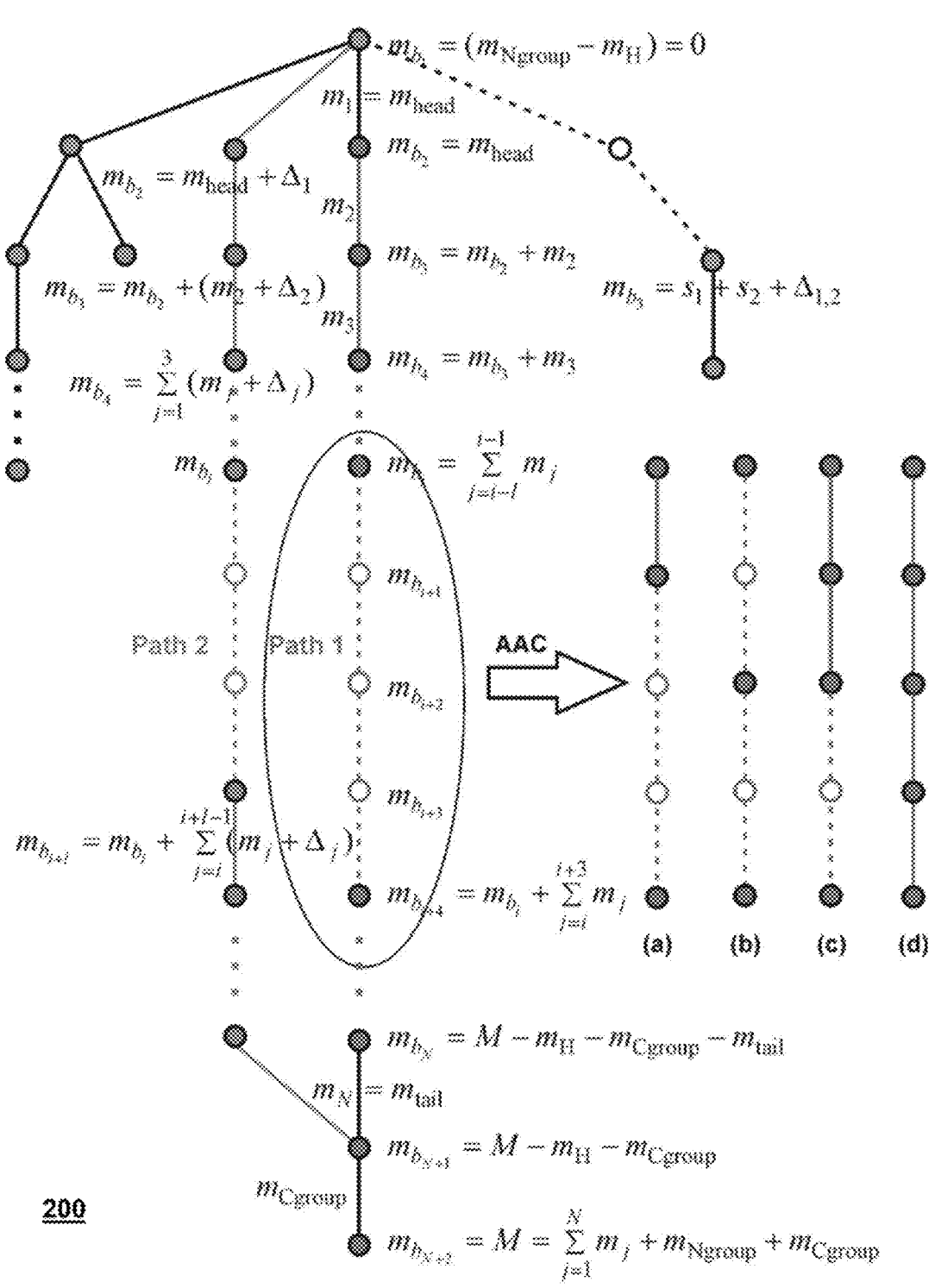
FIG. 4 depicts a spectrum graph illustrating path finding under a graph theory model in accordance with certain embodiments of the present disclosure.

In the step 120, the preprocessed data from the step 110 are used to find valid paths (sequences), and the number n of candidate sequences is counted. Refer to FIG. 4, which depicts a spectrum graph 200 as an example for illustrating the present disclosure. Suppose that $m_{Ngroup} = m_H$ and $m_{Cgroup} = m_{OH}$. The graph theory model is used to find the candidate paths (valid paths) each of which starts with a head mass $m_{head}$ and ends with mass $M - m_H - m_{Cgroup} - m_{tail}$ in a DAG. Since the masses obtained by mass/charge ratio set (m/z) are likely created by b-ion, y-ion, or both b-ion and $\gamma$-ion. A single mass set $$m'_{b,i} \text{ or } m'_{y,i}$$

or both mass sets $$m'_{b,i} \text{ and } m'_{y,i}$$

can be considered in the path-finding algorithm. In the graph model, the mass of the fragment ion can be represented by a vertex. If the mass gap between two fragment ions equals the mass of any amino acid, then an edge is added between these two vertices. As shown in FIG. 4, the tree can be expanded edge by edge. If the set of vertices is complete for the correct path, the sequencing problem can be reduced to finding the longest path in the graph. The path should include both the head and the tail vertices. Moreover, only those paths ending with mass M are taken as candidates. In the example of FIG. 4, only Path 1 and Path 2 are candidate paths.

The selection of suitable mass set(s) for peptide sequencing is strongly based on the peptide design. In one embodiment, F is the head (fixed amino acid at the N-terminus), R or K is the tail (fixed amino acid at the C-terminus) and no P or other basic amino acids in the middle. Previous experimental data shows that the parent ion peak with charge 2 is the strongest peak while the one with charge 3 is very weak, and the y-ions are much stronger than the b-ions when the charge 2 peak were selected for MS/MS. In this case, only the MS/MS spectra from the charge 2 peak would be analysed. Furthermore, using the masses of y-ions would be sufficient to find all sequences and thus only y-ions are used. In another embodiment, H is the head, R is the tail and no P or other basic amino acids in the middle. In this case, the charge 3 peak may be much stronger than, or as strong as the charge 2 peak. The MS/MS spectra of one or both parent peaks would be analysed. When the charge is 2, using the masses of y-ions is sufficient to find all sequences and thus only y-ions are used. However, when the charge is 3, both y- and b-ions are used. In another embodiment, the head and tails are not basic amino acids, the charge is usually 2, and both y- and b-ions would be used.

Due to the imperfect fragmentation in MS/MS characterizations, two and three missing ions are often observed in a sequence. Under the disclosed model of the peptide as considered, in order to ensure that the paths starting from the head can be extended to the tail, the number of missing amino acids is assumed to be up to $L_{AAC}$ in Stage 1. Starting from the mass with $m_{b,1} = 0$, firstly, an attempt is made to find the mass of the head amino acid, $m_{b,2} = m_{head} + \Delta_1$. Next, the mass $m_{b,i+1}$ is found by using the preprocessed data such that the mass gap between the current and the next vertices is approximate to mass $s_i$ or mass summation $$\sum_{v=i}^{i+l=1} s_v$$

(in which $1 \le L_{AAC}$) of up to $L_{AAC}$ amino acids with mass $s_v \in g$ (for $v=1, 2, \ldots, N$), i.e. $m_{b,i+1}=m_{b,i}+(s_i+\Delta_i)$ for two consecutive vertices i and i+1, or $$m_{b,i+l} = m_{b,i} + \left( \sum_{v=i}^{i+l-1} s_v + \Delta_{i,i+l} \right)$$

(where $\Delta_{i,i+l} \in [-l\delta, +l\delta]$ for a length-l tag from Vertex i to Vertex (i+l). Refer to FIG. 4. Suppose that Path 2 is the correct path but with experimental masses, $m_{b,1}=0$, $m_{b,i+1}=m_{b,i}+(m_i+\Delta_i)$ for two consecutive vertices, or $$m_{b,i+l} = m_{b,i} + \sum_{j=i}^{i+l-1} (m_j + \Delta_j)$$

for a length-l tag. If Path 1 is the correct path with theoretical masses, then $m_{b,i+1}=m_{b,i}+m_i$ with $m_{b,1}=M_{Ngroup}-m_H$, $m_{b,2}=(m_{Ngroup}-m_H)+m_{head}, \ldots, m_{b,N}=M-m_H-m_{Cgroup}-m_{tail}$, $m_{b,N+1}=M-m_H-m_{Cgroup}$, and $m_{b,N+2}=M$. Refer to FIG. 4. If the mass gap between two vertices equals the mass of an amino acid, then a solid edge is added. On the other hand, if the mass gap equals the mass summation of two or more amino acids, then the dashed edges are added with hollow circles representing the missing vertices.

In the step 130, the effects of the following five factors are jointly considered when arriving at the score of a sequence candidate from step 131 to step 135: length of consecutive amino acids retrieved (step 131), number of amino acids retrieved (step 132), match error (step 133), average intensity of amino acids retrieved (step 134), and number of occurrences for different ion types with different offsets (step 135). The sequences with the longest length of consecutive amino acids retrieved are first selected (step 131). Among the selected sequences, the sequences with the largest number of amino acids retrieved are then selected (step 132). For the sequences with equal length of consecutive amino acids retrieved together with equal number of amino acids retrieved, the match error is evaluated. As mentioned above, the match error is a mean error between observed mass values for amino acids retrieved from the experimental spectrum and actual mass values of the amino acids normalized by the corresponding observed mass values (step 133). If there are more-than-one sequences having an identical match error, the average intensity of amino acids retrieved is further calculated and a higher score is given to the sequence with a larger average intensity value (step 134). In addition, multiple ion types are usually considered as important factors in inferring an amino acid. It means that a mass value may correspond to different types of ions in the spectrum. Generally, the higher number of occurrences for different ion-types of an amino acid is, the more likely the amino acid is correct. Therefore, for the sequences with equal score after the aforementioned evaluations of the steps 131-134 are performed, the number of occurrences for different ion-types is counted to determine the sequence (step 135). The mass offset sets for the N-terminal a-ion, b-ion and c-ion type sets, i.e. {a, a-$H_2O$, a-$NH_3$, a-$NH_3$—$H_2O$}, {b, b-$H_2O$, b-$H_2O$—$H_2O$, b-$NH_3$, b-$NH_3$—$H_2O$}, and {c, c-$H_2O$, c-$H_2O$—$H_2O$, c-$NH_3$, c-$NH_3$—$H_2O$} are {−27, −45, −44, −62}, {+1, −17, −35, −16, −34}, and {+18, 0, −18, +1, −17}, respectively. The mass offset sets for the C-terminal x-ion and γ-ion type sets can be calculated by shifting the masses of the c-ion and b-ion type sets by +27 and +18, respectively. According to the fragmentation method and the property of the data, all or some of the above ion types can be used flexibly.

The candidate sequences obtained in the step 120 are found by using the preprocessed data, which aim to provide more reliable information to generate the partial sequence. However, when insufficient data is provided by preprocessing, AACs are likely to be present in the candidate sequences. In the step 140, if selected sequences with missing mass values exist, which means that the corresponding mass gaps are equal to the summation of at least two amino acids, the raw data may be used to find as many vertices as possible for the path in Stage 2. For the raw data, suppose that all (m/z) ratios have the opportunity to be created by singly, doubly or triply charged ions. Then the set with q mass/charge ratios $(m/z)_i$, i=1, 2, . . . , q, can be converted to the mass set $m'_b$ of putative b-ion and the equivalent b-ion mass set $m'_y$ of putative y-ion, and each of the sets $m'_y$ and $m'_y$ has 3q elements. Although the number of mass values increases, only the range between the head mass and the tail mass of the AAC is considered and is relatively smaller when compared to that for the whole sequence. As shown in FIG. 4, a gap being the mass summation of 4 amino acids is shown in Path 1. With more information provided by the raw data, the following cases can be found for the gap: (a) composition of amino acid and AAC, (b) composition of two AACs, (c) composition of tag and AAC, and (d) one tag. Note that a gap being the mass summation of more amino acids is effective in ensuring that valid paths can be formed. However, more candidate sequences may be generated and thus a longer time is required for peptide sequencing.

As shown in FIG. 3, after finding the missing amino acids of AACs in step 141, the sequences with the longest length of consecutive amino acids retrieved in AACs are selected as the candidate sequences (step 142). If at least two candidate sequences remain after selection, a final decision is made based on the match error of the amino acids retrieved in AACs for each sequence (step 143).

E. Peptide Sequencing: Highest-Intensity-Tag Based Sequencing Method

The mass/charge (m/z) ratio corresponding to the first or second highest intensity is first recognized to further infer the tag or the path. In the highest-intensity-tag based sequencing method, short tags with three amino acids are used in the tag-based methods, such as GutenTag, DirecTag, and NovoHCD. Although tags with shorter lengths can avoid introducing incorrect amino acids, the number of candidate tags is relatively larger and sometimes it is harder to infer the sequences due to insufficient information provided by the tag. Note that the length of the tag is not fixed and can be up to the length of the peptide if the data is complete, thus helping to reduce the search space. When a tag contains incorrect amino acids, usually it cannot be extended with valid prefix and suffix parts. In this case, the length of the tag is shortened by adaptively reducing the number of the higher-intensity data points used for the tag-finding algorithm. In addition, the vertex with the highest intensity may not definitely be present in the correct path due to uncertainty of the data. When valid paths cannot be found, it may be possible to infer the tag with the second highest intensity.

Figure 5:
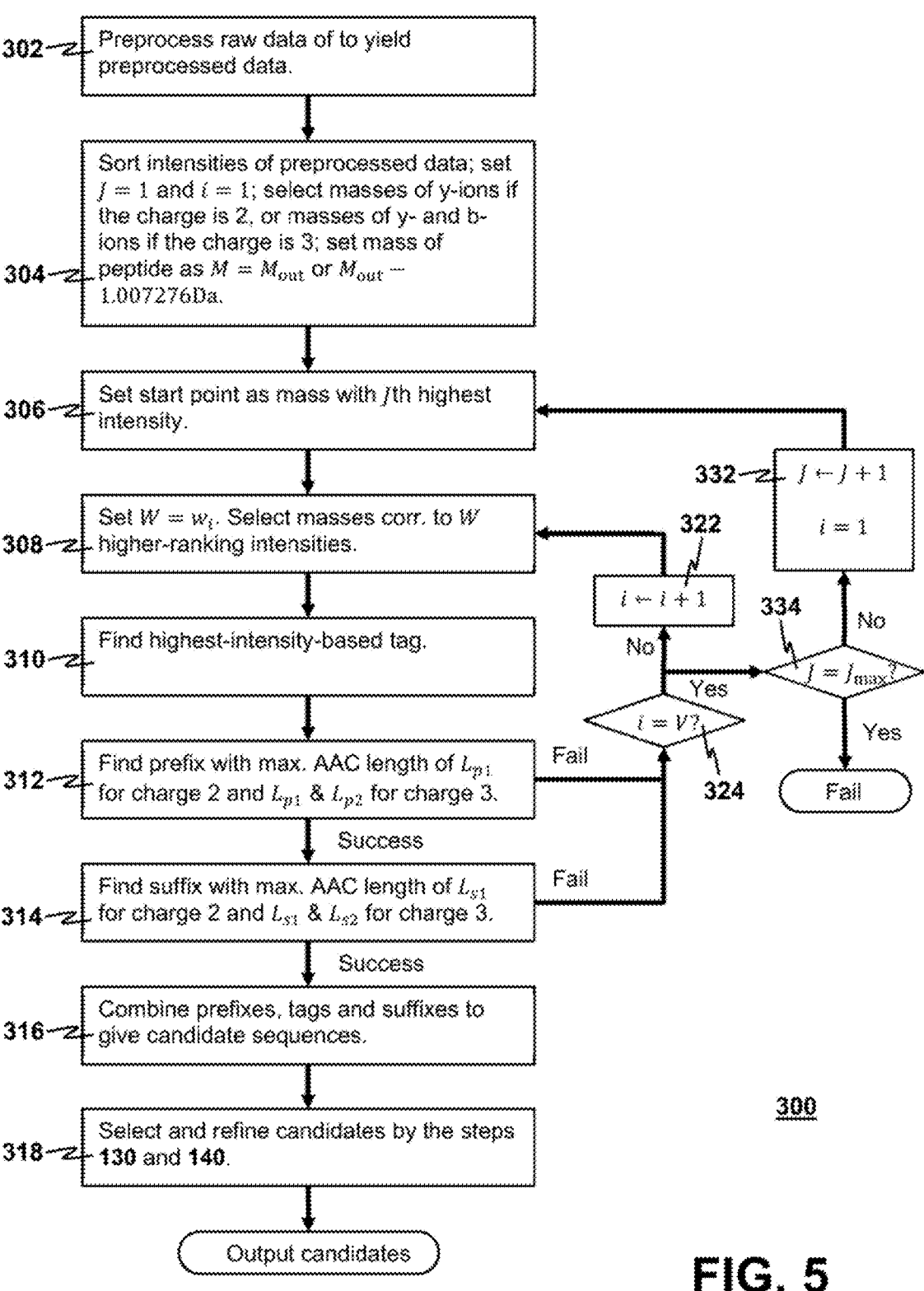
FIG. 5 depicts a flowchart illustrating a method of highest-intensity-tag based sequencing in accordance with certain embodiments of the present disclosure.

FIG. 5 depicts a flowchart showing exemplary steps used in a method 300 of highest-intensity-tag based sequencing. The method 300 commences at step 302 for preprocessing the raw data. The step 302 is the same as the step 110 of the two-stage sequencing method 100. The method 300 then proceeds from the step 302 to steps 304, 306 and 308.

In the steps 304, 306 and 308, the intensities of the preprocessed data are sorted from the largest to the smallest with/denoting the ranking of intensity. The mass/charge ratio with the highest intensity is then identified and the mass/charge ratio is converted to the corresponding mass of a b-ion. As a start, it is set as J=1 and i=1, and only the mass/charge ratio with a higher ranking $W=w_i$ ($w_1> w_2> \ldots >w_y$) is used in tag-finding processing.

In the steps 302 and 304, for each sequence, a preprocessing unit also outputs (i) the selection of the mass set (i.e. set of y-ions, or set of y-ions and b-ions) based on the charge (most often 2 or 3), and (ii) the determination of the mass M ($=M_{out}$ or $M_{out}-1.007276$ Da) of the whole sequence based on the isotopic pattern of the parent ion in a similar fashion as in the preprocessing step (i.e. the step 110) as disclosed above, where $M_{out}$ is the mass output of the mass spectrometer corresponding to the highest intensity, which may be the monoisotopic peak or the peak that follows (with mass +1.007276 Da).

The selection of suitable mass set(s) for peptide sequencing is strongly based on the peptide design. In one embodiment, F is the head (fixed amino acid at the N-terminus), R or K is the tail (fixed amino acid at the C-terminus) and no P or other basic amino acids in the middle. Previous experimental data shows that the parent ion peak with charge 2 is the strongest peak while the one with charge 3 is very weak, and the y-ions are much stronger than the b-ions when the charge 2 peak were selected for MS/MS. In this case, only the MS/MS spectra from the charge 2 peak would be analysed. Furthermore, using the masses of y-ions would be sufficient to find all sequences and thus only y-ions are used. In another embodiment, H is the head, R is the tail and no P or other basic amino acids in the middle. In this case, the charge 3 peak may be much stronger than, or as strong as the charge 2 peak. The MS/MS spectra of one or both parent peaks would be analysed. When the charge is 2, using the masses of y-ions is sufficient to find all sequences and thus only y-ions are used. However, when the charge is 3, both y- and b-ions are used. In another embodiment, the head and tails are not basic amino acids, the charge is usually 2, and both y- and b-ions would be used.

Figure 6:
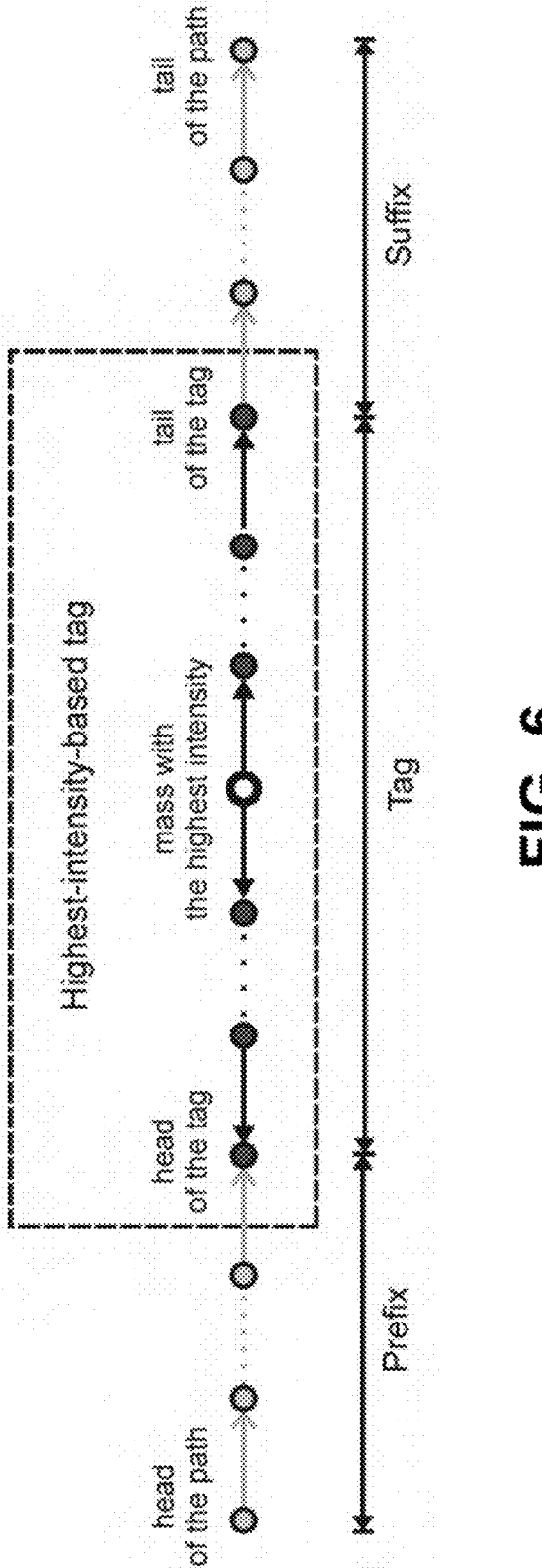
FIG. 6 depicts a conceptual diagram of a candidate sequence as determined by the highest-intensity-tag based sequencing method in accordance with certain embodiments of the present disclosure.

The method 300 then proceeds to step 310 to find the highest-intensity-based tag. Starting from the mass $m'_{B_J}$ of the b-ion or $m'_{Y_J}$ of the y-ion with the highest intensity, the highest-intensity-based tag is found by simultaneously connecting the vertices in the forward direction pointing to the tail vertex of the path and connecting the vertices in the backward direction pointing to the head vertex of the path. Here, the vertices have mass gaps being the mass $g_k$ (k=1, . . . , K) of any amino acid and the length of the tag should be as long as possible (see FIG. 6). The tags containing the amino acid with the highest intensity are obtained subsequently, and are called the highest-intensity-based tags. With knowledge of the masses of the head and the tail amino acids of a highest-intensity-based tag, the method 300 proceeds to step 312 to find the prefixes that can connect the head of the path to the head of the tags in the forward direction by using the method described in the step 120 of the two-stage sequencing method 100. For the tags with valid prefixes, in step 314, the suffix parts of the sequences can be further found by linking the tail of the tags to the tail of the path in the forward direction using a similar method.

Figure 7:
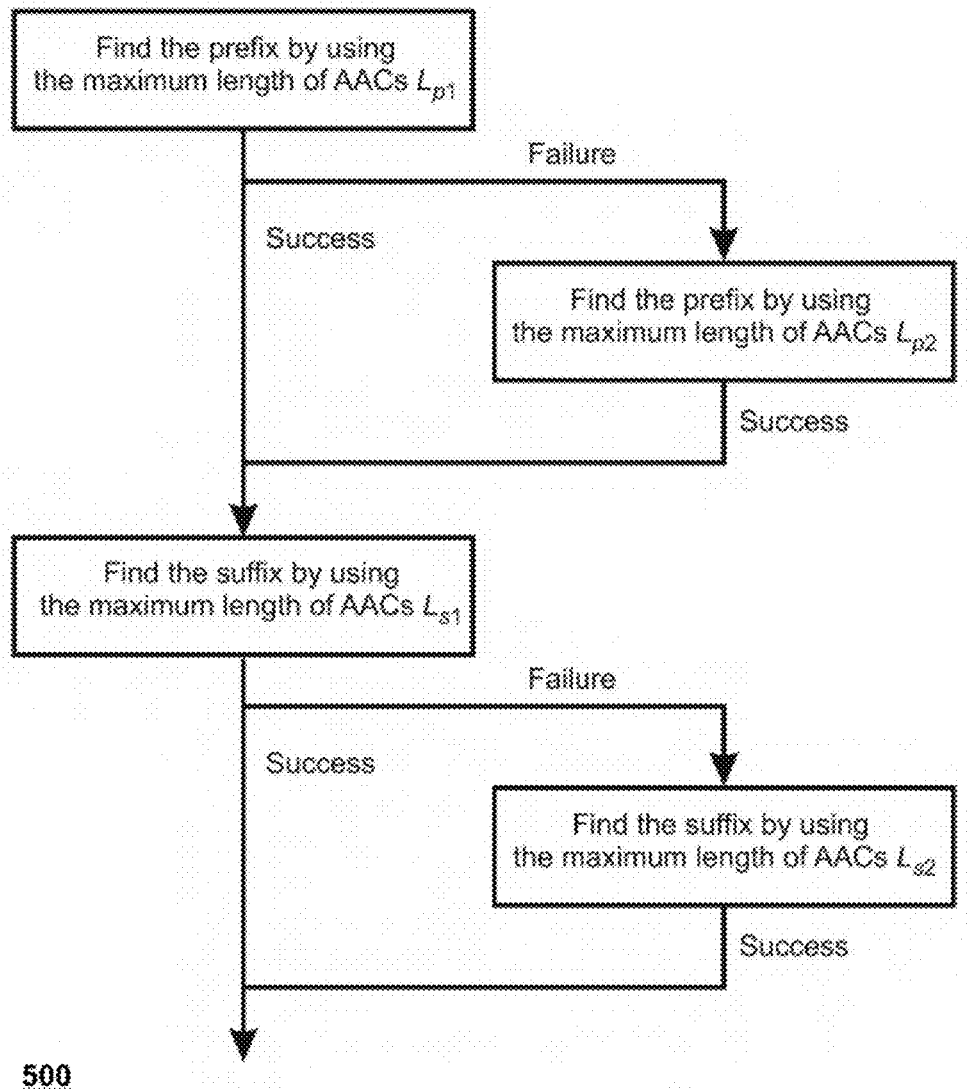
FIG. 7 depicts a flowchart illustrating a first method of finding prefix and suffix of the highest-intensity-based tag to form a possible candidate sequence, where the prefix and suffix are identified based on a maximum length of AACs in accordance with certain embodiments of the present disclosure.
Figure 8:
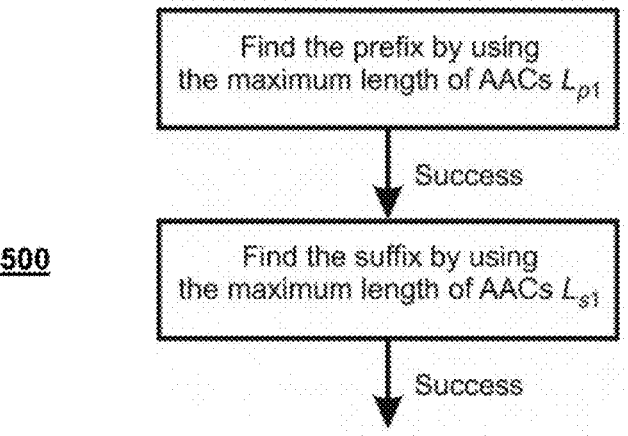
FIG. 8 depicts a flowchart illustrating a second method of finding prefix and suffix of the highest-intensity-based tag to form a possible candidate sequence, where the prefix and suffix are identified based on a maximum length of AACs in accordance with certain embodiments of the present disclosure.

In the prefix and suffix finding process in the steps 312 and 314, it is very important to set the maximum length of AACs properly such that more valid sequences can be found even when some of the masses are not reliable. The maximum length of AACs is set to limit a length of each AAC in the prefix or suffix. The preprocessed data are relatively reliable and provide a mass-intensity pattern for each output mass. Thus, we use the preprocessed data to first find a main path with one or more AACs. Moreover, the path connects the head amino acid for the prefix part, the tail amino acid for the suffix part, and the highest-intensity tag. If the maximum length of AACs is small (for example 3 or 4), then the searching time is short but some of the valid paths may not be found. In case the prefix part or the suffix part cannot be found, we can adjust the maximum length of AACs to a sufficiently large value (for example 10). Details of the prefix- and suffix-finding methods 500 for charge 3 and for charge 2 are illustrated in FIGS. 7 and 8, respectively. Let the two maximum lengths of AACs for the prefix be $L_{p1}$ and $L_{p2}$ with $L_{p2}>L_{p1}$, and the two maximum lengths of AACs for the suffix be $L_{s1}$ and $L_{s2}$ with $L_{s2}>L_{s1}$. As shown in the AAC(b) shown in FIG. 4, after the highest-intensity tag is obtained, we first use $L_{p1}$ to find the prefix. If a prefix cannot be found, we use $L_{p2}$ to find the prefix. After a valid prefix is found, we first use $L_{s1}$ to find the suffix. If it fails, we then use $L_{s2}$. Depending on the property of the spectra, the lengths in each one of the two pairs ($L_{p1}$, $L_{s1}$) and ($L_{p2}$, $L_{s2}$) can be equal or different. For the 4095-sequence data set, we use $L_{p1}=L_{s1}=3$ and $L_{s2}=10>L_{p2}=6$. When the charge is 2, only $L_{p1}$ and $L_{s1}$ are considered, as shown in FIG. 7.

In step 316, the candidate paths can be constructed by combining the three parts: prefix, tag, and suffix. In step 318, one can follow the steps 130 and 140 of the two-stage sequencing method 100 to select and refine the sequences. Note that a larger value used for W sometimes introduces one or more incorrect amino acids in the head and/or tail parts of a tag, while a smaller value used for W may give a more reliable tag but the length of the tag may be limited. Therefore, in steps 322 and 324, if no valid candidates can be found, one may attempt to reduce the value of W with $W=w_i$ by increasing i by one, i.e. i⊖i+1, and repeat the tag-prefix-suffix finding procedure until the candidate sequence can be found or i=V is reached (where V is the maximum number of iterations).

In steps 332 and 334, when the experimental mass with the highest intensity gives an unreliable message due to noise and uncertainty, a highest-intensity-based tag or a valid path with the highest-intensity-based tag is not found. In this case, the mass with the second highest intensity is used, by setting J⊖J+1 and i=1, to find the second highest-intensity-based tag and the candidates. This process continues until the sequence is found or $J=J_{max}$ is reached (where $J_{max}$ is the maximum number of higher-ranking-intensity masses allowed to be the start point to find the tag).

In some embodiments, both y-ions and b-ions are considered in the sequencing as described above. To reduce the searching space and improve the accuracy for the sequencing, we consider the following three steps for the selection of the mass set: (1) selecting the mass ranges for both y-ions and b-ions; (2) eliminating the mass overlap between y-ions and b-ions; and (3) avoiding two masses representing the same peak of the spectrum coexisting in the path.

Step 1. We use the masses of both y-ions and b-ions for sequencing. Depending on the properties of the spectra, we can select: (i) some of the masses of y-ions and some of the masses of b-ions; (ii) all masses of y-ions and some of the masses of b-ions; (iii) some of the masses of y-ions and all masses of b-ions; or (iv) all masses of y-ions and b-ions. When more masses of y-ions and/or b-ions are used, more noise and interference is introduced into the sequencing.

Hence, we use as few mass values as possible with an aim to ensure that the valid sequences include the correct sequence. In other words, Case (i) as mentioned above is preferred.

In Case (i), the mass set m' used to find the path is then given by $$m' = \{m'_b, m'_y\} = \{m'_{b,1}, m'_{b,2}, \dots, m'_{b,L}, m'_{y,1}, m'_{y,2}, \dots, m'_{y,L}\}.$$

For the peptides in the 4095-sequence data set as described above, it has been observed that the second half part of the full path can be obtained by using the masses of y-ions, while the first half part is mainly found by using the masses of b-ions. If the mass set is $$m' = \{m'_{b,1}, m'_{b,2}, \dots, m'_{b,u}, m'_{y,u+1}, m'_{y,u+2}, \dots, m'_{y,L}\},$$

then the path does not contain both mass $m'_{b,i}$ and $m'_{y,i}$ for each i=1, 2, . . . , L. One simple setting method is to set u such that $m'_{b,u}$ is the largest value approaching M/2. Then the mass set m' used to find the path contains the masses of b-ions in $m'_b$ below M/2 and the masses of y-ions in $$m'_y$$

beyond or equal to M/2, i.e.

$$m'_{b,i} < M/2 \text{ for } i = 1, 2, \dots, u \text{ and } m'_{y,} \geq M/2 \text{ for } i = u+1, u+2, \dots, L.$$

Step 2. For some spectra, using only the masses in set $\{m'_{b,1}, m'_{b,2}, \dots, m'_{b,u}\}$ with $$m'_{b,i} < M/2 \text{ for } i = 1, 2, \dots, u$$

cannot fully cover the range of the first half of the path, and hence some information of y-ions is needed to obtain one or two correct masses located near M/2. Here we adjust the mass set for sequencing and include the masses of y-ions $$m'_{y,i} \geq M/2 - e$$

(here we set e=200) for i=v+1, v+2, . . . , L and the masses of b-ions $$m'_{b,i} < M/2 \text{ for } i = 1, 2, \dots, u,$$

i.e. $m' = \{m'_{b,1}, m'_{b,2}, \dots, m'_{b,u}, m'_{y,v}, m'_{y,v+1}, \dots, m'_{y,u}, m'_{y,u+1}, \dots, m'_{y,L}\}$ with u>v. The masses of the b-ions may overlap with the masses of the y-ions in the range from mass M/2−e to M/2, which implies that different peaks of the spectrum generate the same mass, i.e.

$$m'_{b,i} = m'_{y,i}.$$

We suppose that the mass pairs $$P_1 = \{m'_{y,i}, m'_{y,+1}\}, P_2 = \{m'_{y,i}, m'_{b,i+1}\},$$

$$P_3 = \{m'_{b,i}, m'_{y,i,+1}\} \text{ and } P_4 = \{m'_{b,i}, m'_{b,i+1}\}$$

are present in the spectrum when $m'_{b,i}=m'_{y,i}$ and $m'_{b,i+1}=m'_{y,i+1}$. Then we merge the four pairs $P_1 \sim P_4$ into one pair. Generally, there is a deviation between the experimental and the theoretical masses. Then we give priority according to $P_1 > P_4 > P_3 > P_2$. When all four pairs are found, we select the mass pair $P_1$ and remove pairs $P_2$, $P_3$ and $P_4$. Similarly, if only the two mass pairs $P_2$ and $P_4$ (or $P_3$ and $P_4$) are found, we keep $P_4$ only.

Step 3. According to the antisymmetric requirement [Sherenga], only mass $$m'_{b,i} \text{ or } M - m'_{b,i}(m'_{y,i} \text{ or } M - m'_{y,i})$$

can be present in the path to avoid occurrence of the same peak two times in a spectrum. Suppose that mass $$m'_{b,i}(\text{or } m'_{y,j})$$

is one of the masses for the tag. We remove mass $$M - m'_{b,j}(\text{or } M - m'_{v,j})$$

in set m' to further find the prefix part. Next, suppose that mass $$m'_{b,k}(\text{or } m'_{y,k})$$

is one of the masses for the prefix part. We remove mass $$M - m'_{b,k}(\text{or } M - m'_{y,k})$$

in set m' and continue to find the suffix part.

In the above descriptions of the steps 304 and 306, all the masses of a peptide and the corresponding calculations are assumed to be precise. In practice, the masses given by the spectra have a tolerance and hence all calculations are performed within a tolerance range.

F. Checking Method Based on the Design of the Sequences

Figure 9:
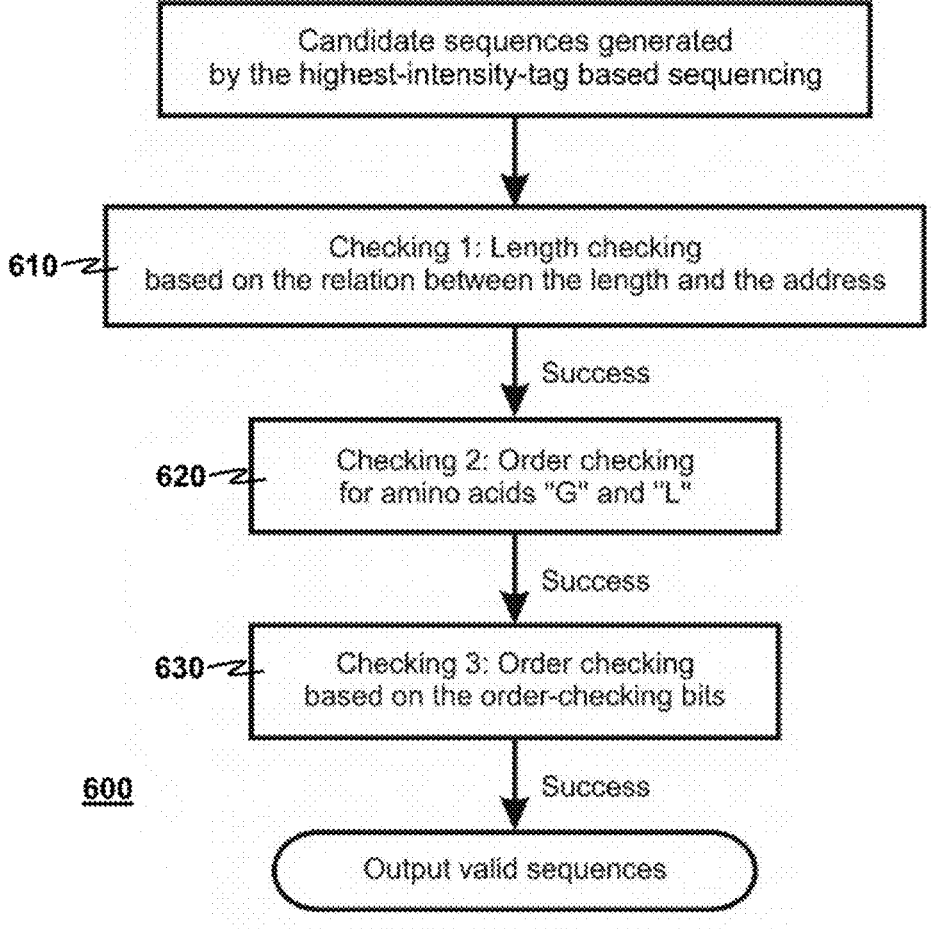
FIG. 9 depicts a flowchart illustrating a checking method for candidate sequences in accordance with embodiments of the disclosure.

FIG. 9 shows an illustration of the checking method 600 for the candidate sequences. For each candidate sequence obtained by using the highest-intensity-based tag sequencing method 300, we perform the following three checking steps based on the design of the peptides.

First, the length of a sequence can be 15, 16, 17, 18 or 19. As mentioned above in the design of the peptide sequences, the length of a sequence is directly related to its address in the whole block. Thus, the validation of a sequence can be determined by (i) evaluating an expected length of the sequence based on its address and (ii) comparing the expected length and the actual length. This checking is shown as checking step 610 in FIG. 9.

Second, if there exists an output sequence with a valid length and the sequence contains the amino acid "L", the order of the amino acids "G" and "L" will be further checked. This checking is shown as checking step 620 in FIG. 9. We first find the position $P_L$ of the last amino acid "L" and the position $P_G$ of the first amino acid "G", and then compare $P_L$ with $P_G$. If $P_L > P_G$, then the sequence is not valid and is to be discarded.

Third, if a sequence can be found successfully, we perform an order check based on the order-checking bits of the sequence. This checking is shown as checking step 630 in FIG. 9. According to the orders of the estimated symbol pairs $\{S_1, S_2\}$, $\{S_2, S_3\}$ and $\{S_{L-1}, S_L\}$, the order-checking bits are generated based on the pre-defined rules. The generated order-checking bits are compared against the corresponding bits in the estimated symbol $S_5$ to see if they are identical. As an example, if there is no error in the orders of $S_1$ and $S_2$, the generated order-checking bit for $\{S_1, S_2\}$ should match the first bit of the estimated symbol $S_5$. If the generated order-checking bits do not match all three bits of $S_5$ in the estimated sequence, the estimated sequence in the block should be removed.

Finally, if the sequence can pass all three checking processes, we output this sequence as a valid sequence.

Note that the three checking steps 610, 620, 630 may be performed in any order, not strictly in the above-mentioned order as shown in FIG. 9. In addition, not all three checking steps 610, 620, 630 may be used together in verification. Any combination of one or more of the three checking steps 610, 620, 630 may be used.

Although the checking method 600 is illustrated for use in the highest-intensity-based tag sequencing method 300, it is possible to use the checking method 600 for applications in the two-stage sequencing method 100. Nonetheless, some of the checking steps 610, 620, 630 may be required to be adapted for the two-stage sequencing method 100. For instance, it is possible that the requirement of a certain length may be observed even during the search for valid paths in the step 120. The checking step 610 may not be necessary to be implemented in certain practical situations.

G. Sample Data

Figure 10:
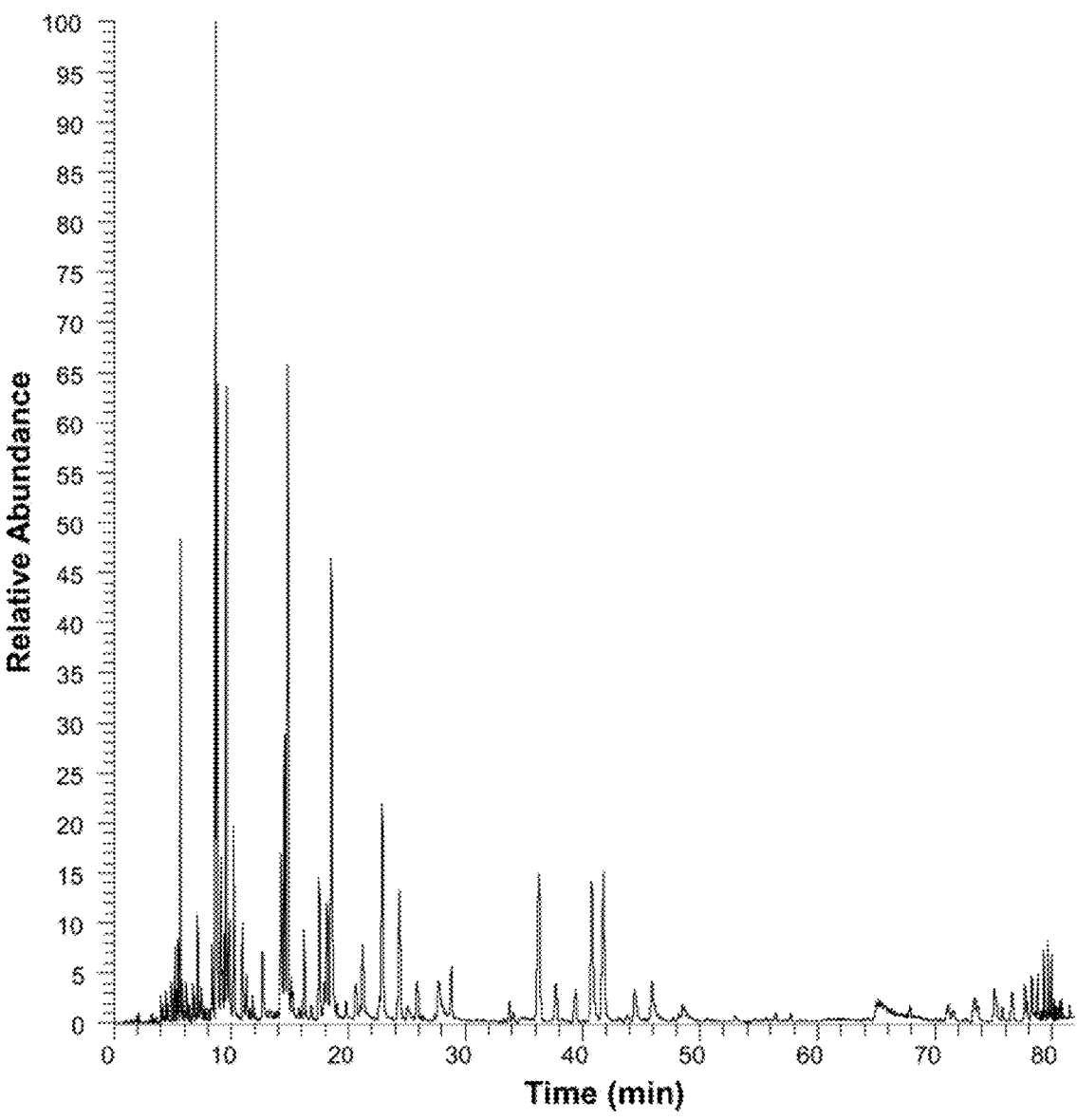
FIG. 10 depicts a TIC of an example mixture of data-encoding peptides as obtained from an experiment.

A peptide mixture encoded using the first 50 addresses in the 4095 peptides block as described above with F as head and R as tail (sequence details shown in Table 3) was sequenced using the method described above. The TIC of the mixture is shown in FIG. 10. All peptides were correctly sequenced.

TABLE 3

Sequence details of the 50 peptides.

| ID | Sequence | Monoisotopic Mass |
|---|---|---|
| 1 | FGFVSEYYYYTVGSTAR (SEQ ID NO: 1) | 2008.92071 |
| 2 | FFEYGGYYYTSYFGYEGR (SEQ ID NO: 2) | 2267.94764 |
| 3 | FTFVYEYYYEYVYVYFEAR (SEQ ID NO: 3) | 2613.17806 |
| 4 | FVAVLVYYYVSSETVLFGER (SEQ ID NO: 4) | 2340.20423 |
| 5 | FYTFGYYYYAGFTFTTESYAR (SEQ ID NO: 5) | 2617.14781 |
| 6 | FEYFESYYYSVVAGFFR (SEQ ID NO: 6) | 2172.98332 |
| 7 | FVLVVEYYYGGGSTSTFR (SEQ ID NO: 7) | 2043.99422 |
| 8 | FSFAAEYYYFFETYSFEFR (SEQ ID NO: 8) | 2513.08924 |
| 9 | FTYEVSYYTYFYSTGSAGAR (SEQ ID NO: 9) | 2332.03244 |
| 10 | FFTFTSYYTTASAGGTVEAER (SEQ ID NO: 10) | 2305.0539 |
| 11 | FEFVTVYYTEAATAAYR (SEQ ID NO: 11) | 2000.952 |
| 12 | FALVTVYYTVAYGASSER (SEQ ID NO: 12) | 1995.99421 |
| 13 | FVTTYFYYTAEFSEASEYR (SEQ ID NO: 13) | 2373.04776 |
| 14 | FYVGFTYYTSVAFFFEYFAR (SEQ ID NO: 14) | 2524.17801 |
| 15 | FFYGTAYYTGVVFVFYAVYVR (SEQ ID NO: 15) | 2531.2566 |
| 16 | FTTSTAYYTFYTFTVFR (SEQ ID NO: 16) | 2114.99898 |
| 17 | FFYAESYYEYLEYVVFER (SEQ ID NO: 17) | 2416.09399 |
| 18 | FGEAYSYYETSGFFVYGVR (SEQ ID NO: 18) | 2241.0055 |
| 19 | FTAYTEYYEESSSSFAETGR (SEQ ID NO: 19) | 2323.9757 |
| 20 | FFFAEFYYEVTFESEYEGGER (SEQ ID NO: 20) | 2645.12746 |
| 21 | FSVETGYYEAYGEEYTR (SEQ ID NO: 21) | 2062.87961 |
| 22 | FVFEFEYYESYYEYAVAR (SEQ ID NO: 22) | 2374.04703 |
| 23 | FVVGASYYEGYYASYSSER (SEQ ID NO: 23) | 2196.96402 |
| 24 | FGAFGSYYEFEGVVTESAVR (SEQ ID NO: 24) | 2214.02696 |
| 25 | FYEVAYYYVYYSVVTSLAYER (SEQ ID NO: 25) | 2647.25229 |

TABLE 3-continued

Sequence details of the 50 peptides.

| ID | Sequence | Monoisotopic Mass |
|---|---|---|
| 26 | FSTTSGYYVTFSYGEGR (SEQ ID NO: 26) | 1920.85302 |
| 27 | FVAVAVYYVEFAVYYSYR (SEQ ID NO: 27) | 2208.09321 |
| 28 | FYTAEYYYVVESGESFYTR (SEQ ID NO: 28) | 2373.04776 |
| 29 | FEETAFYYVAFGASAYVSAR (SEQ ID NO: 29) | 2248.04769 |
| 30 | FYGVEEYYVSAVTTYSGEYFR (SEQ ID NO: 30) | 2529.13764 |
| 31 | FFEVFSYYVGATTSAYR (SEQ ID NO: 31) | 2006.94145 |
| 32 | FETAFSYYVFFVEGFAVR (SEQ ID NO: 32) | 2178.04626 |
| 33 | FSVASSYYAYESTVYVAVR (SEQ ID NO: 33) | 2161.03681 |
| 34 | FGVEEFYYATVVTYGGSSER (SEQ ID NO: 34) | 2260.03244 |
| 35 | FEEFYSYYAESSGTFGAAVVR (SEQ ID NO: 35) | 2379.06955 |
| 36 | FGYGVSYYAVTTESETR (SEQ ID NO: 36) | 1928.87923 |
| 37 | FEAAYEYYAAYTAGGEAR (SEQ ID NO: 37) | 2001.87444 |
| 38 | FAFEYEYYASFAEVGTTVR (SEQ ID NO: 38) | 2249.03171 |
| 39 | FEVFYTYYAGAAAEFGGFER (SEQ ID NO: 39) | 2294.03203 |
| 40 | FLVATAYYAFVEYLVVVAESR (SEQ ID NO: 40) | 2409.26207 |
| 41 | FEGVSEYYSYFSSVAGR (SEQ ID NO: 41) | 1946.86867 |
| 42 | FVYTSSYYSTTFVAGEER (SEQ ID NO: 42) | 2105.95822 |
| 43 | FSVTLFYYSELAFEVFFYR (SEQ ID NO: 43) | 2427.18277 |
| 44 | FATVESYYSVGAFVEASSTR (SEQ ID NO: 44) | 2170.02188 |
| 45 | FSAFYSYYSAEEEFSAYAVTR (SEQ ID NO: 45) | 2487.09068 |
| 46 | FAVVVGYYSSETVYEAR (SEQ ID NO: 46) | 1938.93636 |
| 47 | FTYAESYYSGSTGATETR (SEQ ID NO: 47) | 1989.85921 |
| 48 | FTSAVEYYSFEGSVYESGR (SEQ ID NO: 48) | 2176.95894 |
| 49 | FLEAAAYYLYVTFSVSAYVR (SEQ ID NO: 49) | 2332.178 |
| 50 | FYGTAEYYGTEEFESGTYYER (SEQ ID NO: 50) | 2561.05467 |

H. Details of Embodiments of Present Disclosure

Embodiments of the present disclosure are elaborated as follows based on the details, examples, applications, etc., of the two-stage sequencing method 100, the highest-intensity-tag based sequencing method 300 and the checking method 600 as disclosed above.

An aspect of the present disclosure is to provide a computer-implemented method for sequencing a data-encoded peptide from an experimental spectrum. The method provides one of the following three outputs. In the first output, which corresponds to the best case, an estimate of a peptide sequence is uniquely determined in sequencing the data-encoded peptide. In the second output, plural estimates of the peptide sequence are resulted. In the third output, no estimate is found.

FIG. 11 depicts a flowchart showing exemplary steps of the disclosed computer-implemented method (referenced as 1100 for convenience). The method 1100 comprises steps 1110, 1120, 1130, 1140 and 1150.

Figure 12:
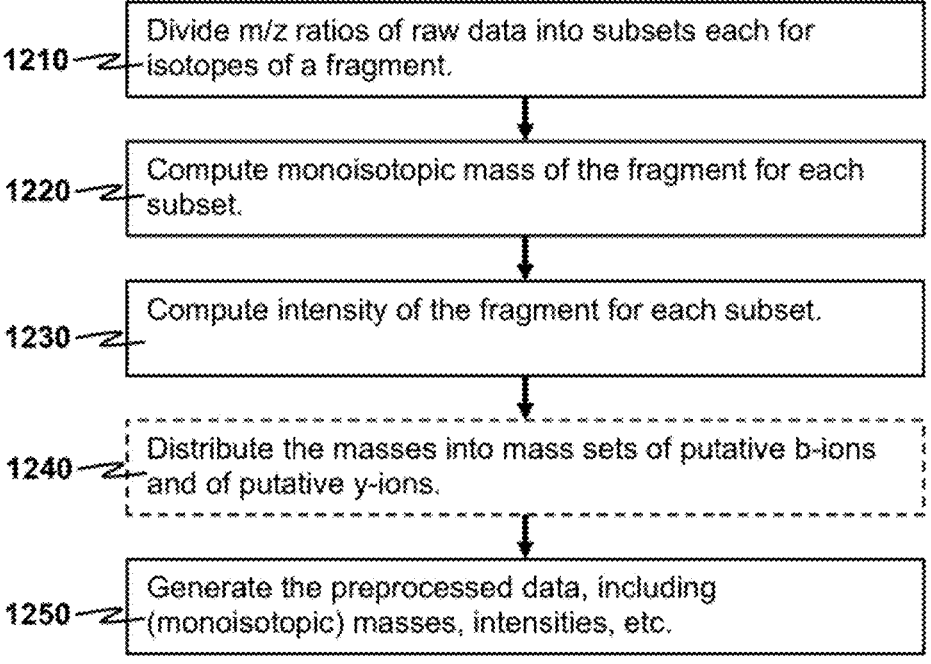
FIG. 12 depicts a flowchart illustrating exemplary steps of processing raw data of experimental spectrum to generate preprocessed data.

In the step 1110, raw data of the experimental spectrum are preprocessed for removing uninterpretable peaks to yield preprocessed data. As mentioned above, the raw data of the experimental spectrum are data of a histogram of intensity versus mass/charge ratio as originally obtained in analyzing the data-encoded peptide by mass spectrometry. The step 1110 corresponds to the step 110 of the two-stage sequencing method 100 and the step 302 of the highest-intensity-tag based sequencing method 300. The step 1110 is further elaborated with the aid of FIG. 12, which depicts a flowchart showing exemplary steps executed in the step 1110.

Exemplarily, the step 1110 comprises steps 1210, 1220, 1230 and 1250. In the step 1210, a set of mass/charge ratios of the raw data is divided into a plurality of subsets where each mass/charge ratio has a signal peak in the experimental spectrum. An individual subset consists of mass/charge ratios of isotopes of a fragment of the data-encoded peptide. In addition, the isotopes of the fragment have a same charge of positive integer value. Usually, the charge has a value of 1, 2 or 3. A monoisotopic mass of the fragment is then computed for the individual subset in the step 1220. An intensity of the fragment is also computed in the step 1230 according to intensities associated with the mass/charge ratios in the individual subset. For instance, the intensity of the fragment may be computed by summing intensity values associated with different mass/charge ratios in the individual subset. The steps 1220 and 1230 are repeated for the plurality of subsets. In the step 1250, the preprocessed data are generated. The preprocessed data includes a plurality of masses and a plurality of intensities. The plurality of masses is formed with the monoisotopic mass of the fragment for the individual subset. An individual mass in the plurality of masses is associated with a corresponding intensity in the plurality of intensities.

Preferably, the preprocessed data further includes a first mass set of putative b-ions and a second mass set of putative y-ions for the experimental spectrum. The step 1110 further comprises a step 1240 of distributing respective masses in the plurality of masses into the first and second mass sets before executing the step 1250.

Refer to FIG. 11. After the preprocessed data are obtained in the step 1110, a first set of one or more candidate sequences contending for a peptide sequence of the peptide is identified from a spectrum graph in the step 1120, where the spectrum graph is formed according to the preprocessed data rather than the raw data. As a result, a fewer number of candidate sequences is generated, thereby advantageously reducing a time cost in sequencing. The step 1120 corresponds to the step 120 of the two-stage sequencing method 100 and the steps 304, 306, 308, 310, 312, 314 and 316 of the highest-intensity-tag based sequencing method 300.

After the first candidate-sequence set is obtained in the step 1120, the first candidate-sequence set is processed in the step 1130 to estimate the peptide sequence.

After a set of one or more estimates of the peptide sequence is obtained, it is desirable to verify whether each estimate is valid such that any invalid estimate of the peptide sequence can be eliminated. The step 1140 is to verify whether an individual peptide-sequence estimate is invalid. In the step 1140, whether the individual peptide-sequence estimate is invalid may be determined by: checking a length of the individual peptide-sequence estimate against a predetermined correct length of the peptide sequence; performing order checking for amino acids "G" and "L" in the individual peptide-sequence estimate; performing order checking based on order-checking bits carried in the data-encoded peptide; or any combination thereof. In the step 1150, the set of one or more estimates of the peptide sequence is purged to remove any peptide-sequence estimate found to be invalid in the step 1140.

Preferably, an individual candidate sequence in the first candidate-sequence set is identified in the step 1120 based on searching over appropriate mass set(s). If a parent ion peak identified in the experimental spectrum has a charge of value 2, preferably an individual candidate sequence in the first candidate-sequence set is identified or determined via searching over the second mass set. If the charge of the parent ion peak is of value 3, the individual candidate in the first candidate-sequence set is identified via searching over the first and second mass sets.

The step 1120 comprises the steps 130 and 140, and is detailed as follows.

If the first candidate-sequence set consists of a single candidate sequence, the single candidate sequence in the first candidate-sequence set is assigned as one estimate of the peptide sequence. Otherwise, one or more candidate sequences are selected from the first candidate-sequence set to form a second set of one or more candidate sequences such that the one or more candidate sequences in the second candidate-sequence set are more probable to be the peptide sequence than non-selected candidate sequences in the first candidate-sequence set (step 130).

If the second candidate-sequence set consists of a single candidate sequence, the single candidate sequence in the second candidate-sequence set is then assigned as one estimate of the peptide sequence.

If the second candidate-sequence set consists of plural candidate sequences that are free from any AAC, the plural candidate sequences in the second candidate-sequence set are then assigned as estimates of the peptide sequence.

If the second candidate-sequence set consists of plural candidate sequences that include one or more AACs, the raw data are then used to determine valid amino-acid sequences for the one or more AACs. After the valid amino-acid sequences are determined, the candidate sequences in the second candidate-sequence set are refined to generate a third set of one or more candidate sequences. The third candidate-sequence set is obtained from the second candidate-sequence set by using the determined valid amino-acid sequences to substitute the one or more AACs and then discarding any candidate sequence with an undetermined AAC (step 141).

If the third candidate-sequence set consists of a single candidate sequence, the single candidate sequence in the third candidate-sequence set is then assigned as one estimate of the peptide sequence. Otherwise, one or more candidate sequences are selected from the third candidate-sequence set to form a fourth set of one or more candidate sequences such that the one or more candidate sequences in the fourth candidate-sequence set are more probable to be the peptide sequence than non-selected candidate sequences in the third candidate-sequence set (steps 142 and 143).

If the fourth candidate-sequence set consists of a single candidate sequence, the single candidate sequence in the fourth candidate-sequence set is then assigned as one estimate of the peptide sequence. Otherwise, plural candidate sequences in the fourth candidate-sequence set are assigned as estimates of the peptide sequence.

In certain embodiments, the step 130 is set forth as follows. First, one or more candidate sequences with a longest length of consecutive amino acids among the candidate sequences in the first candidate-sequence set are selected to form a fifth candidate-sequence set (step 131). If the fifth candidate-sequence set consists of a single candidate sequence, then the fifth candidate-sequence set is assigned to be the second candidate-sequence set. Otherwise, one or more candidate sequences with a largest number of amino acids among plural candidate sequences in the fifth candidate-sequence set are selected to form a sixth candidate-sequence set (step 132). If the sixth candidate-sequence set consists of a single candidate sequence, then the sixth candidate-sequence set is assigned to be the second candidate-sequence set. Otherwise, one or more candidate sequences with a smallest match error among plural candidate sequences in the sixth candidate-sequence set are selected to form a seventh candidate-sequence set (step 133). If the seventh candidate-sequence set consists of a single candidate sequence, then the seventh candidate-sequence set is assigned to be the second candidate-sequence set. Otherwise, one or more candidate sequences with a highest average intensity value of retrieved amino acids among plural candidate sequences in the seventh candidate-sequence set are selected to form an eighth candidate-sequence set (step 134). If the eighth candidate-sequence set consists of a single candidate sequence, then the eighth candidate-sequence set is assigned to be the second candidate-sequence set. Otherwise, one or more candidate sequences with a highest number of occurrences for different ion types with different offsets among plural candidate sequences in the eighth candidate-sequence set are selected to form the second candidate-sequence set (step 135).

In certain embodiments, the step 140 is set forth as follows. One or more candidate sequences from the third candidate-sequence set and with a largest number of amino acids among the determined valid amino-acid sequences are selected to form a ninth candidate-sequence set (step 142). If the ninth candidate-sequence set consists of a single candidate sequence, then the ninth candidate-sequence set is assigned to be the fourth candidate-sequence set. Otherwise, one or more candidate sequences from the ninth candidate-sequence set and with a smallest match error among the determined valid amino-acid sequences are selected to form the fourth candidate-sequence set (step 143).

The step 1120 may be realized as the step 120. In certain embodiments, the step 1120 is set forth as follows.

One or more paths that are valid and that have a longest length in the spectrum graph are first identified, where a valid path begins at a head vertex, and ends at a tail vertex with a mass of the data-encoded peptide. Each of the identified one or more paths is then used to generate a new candidate sequence. The new candidate sequence is allocated to the first candidate-sequence set, unless the new candidate sequence is discarded due to some additional consideration.

The step 1120 may be realized as the steps 304, 306, 308, 310, 312, 314 and 316. In certain embodiments, the step 1120 is set forth with the following steps.

Step A. Sort the plurality of masses in a descending order of corresponding intensities of respective masses to thereby form an ordered sequence of masses, where the ordered sequence of masses ranks the plurality of masses with a highest-ranking mass being associated with a highest corresponding intensity (step 304).

Step B. Given a selected mass and a selected number of higher-ranking masses in the ordered sequence of masses, identify one or more highest-intensity-based tags in the spectrum graph (step 310). An individual highest-intensity-based tag is a partial sequence consisting of a first amino acid having the selected mass and a plurality of remaining amino acids each having a mass selected from the selected number of higher-ranking masses.

Step C. Process the one or more highest-intensity-based tags. Particularly, processing the individual highest-intensity-based tag includes the following tasks: determining a prefix and a suffix for the individual highest-intensity-based tag (steps 312 and 314); if the prefix and suffix are successfully determined, then combining the prefix, the individual highest-intensity-based tag and the suffix to form a new candidate sequence (step 316); and allocating the new candidate sequence to the first candidate-sequence set.

In determining the prefix, preferably the prefix is identified as a first path that is valid and that has a longest length in the spectrum graph, where the first path connects a head amino acid and a head of the individual highest-intensity-based tag, and one or more first AACs with a total length at most a first maximum length are allowable to be present in the identified first path. If the charge of the parent ion peak is of value 2, preferably the first maximum length is set as $L_{p1}$ in determining the prefix. If the charge of the parent ion peak is of value 3, it is preferable that the first maximum length is initially set as $L_{p1}$ in finding the first path, and is relaxed to $L_{p2}$ with $L_{p2}>L_{p1}$ in case finding the first path under the first maximum length being $L_{p1}$ fails.

In determining the suffix, preferably the suffix is identified as a second path that is valid and that has a longest length in the spectrum graph, where the second path connects a tail of the individual highest-intensity-based tag and a tail amino acid, and one or more second AACs with a total length at most a second maximum length are allowable to be present in the identified second path. If the charge of the parent ion peak is of value 2, preferably the second maximum length is set as $L_{s1}$. If the charge of the parent ion peak is of value 3, it is preferable that the second maximum length is initially set as $L_{s1}$ in finding the second path, and is relaxed to $L_{s2}$ with $L_{s2}>L_{s1}$ if finding the second path under the second maximum length being $L_{s1}$ fails.

Step D. Sequentially use successive values in a strictly decreasing sequence of values as the selected number of higher-ranking masses to repeat Steps B and C until the first candidate-sequence set is not empty or the strictly decreasing sequence is exhausted (steps 322 and 324).

Step E. Starting from the highest-ranking mass, sequentially use successive masses in the ordered sequence of masses as the selected mass to repeat Steps B-D until the first candidate-sequence set is not empty or a preselected number of higher-ranking masses in the ordered sequence of masses is reached (steps 332 and 334). The preselected number is $J_{max}$.

The disclosed computer-implemented method is realizable by a computer system with appropriate programming. The computer system is implemented with one or more computers. An individual computer may be a general-purpose computer, a workstation, a computing server, a distributed server in a computing cloud, a notebook computer, a mobile computing device, etc.

The present disclosure may be embodied in other specific forms without departing from the spirit or essential characteristics thereof. The present embodiment is therefore to be considered in all respects as illustrative and not restrictive. The scope of the invention is indicated by the appended claims rather than by the foregoing description, and all changes that come within the meaning and range of equivalency of the claims are therefore intended to be embraced therein.

---

What is claimed is:

1. A computer-implemented method for sequencing a data-encoded peptide from an experimental spectrum, raw data of the experimental spectrum being data of a histogram of intensity versus mass/charge ratio as originally obtained in analyzing the data-encoded peptide by mass spectrometry, the method comprising:

preprocessing the raw data for removing uninterpretable peaks to yield preprocessed data;

identifying, from a spectrum graph, a first set of one or more candidate sequences contending for a peptide sequence of the peptide, wherein the spectrum graph is formed according to the preprocessed data rather than the raw data for generating a fewer number of candidate sequences to thereby reduce a time cost in sequencing;

processing the first candidate-sequence set to estimate the peptide sequence;

after a set of one or more estimates of the peptide sequence is obtained, verifying whether an individual peptide-sequence estimate is invalid; and purging the set of one or more estimates of the peptide sequence to remove any peptide-sequence estimate found to be invalid;

wherein the identifying of the first candidate-sequence set from the spectrum graph comprises:

if the first candidate-sequence set consists of a single candidate sequence, then assigning the single candidate sequence in the first candidate-sequence set as one estimate of the peptide sequence, else selecting one or more candidate sequences from the first candidate-sequence set to form a second set of one or more candidate sequences such that the one or more candidate sequences in the second candidate-sequence set are more probable to be the peptide sequence than non-selected candidate sequences in the first candidate-sequence set;

if the second candidate-sequence set consists of a single candidate sequence, then assigning the single candidate sequence in the second candidate-sequence set as one estimate of the peptide sequence;

if the second candidate-sequence set consists of plural candidate sequences that are free from any amino acid combination (AAC), then assigning the plural candidate sequences in the second candidate-sequence set as estimates of the peptide sequence;

if the second candidate-sequence set consists of plural candidate sequences that include one or more AACs, then using the raw data to determine valid amino-acid sequences for the one or more AACs;

after the valid amino-acid sequences are determined, refining the candidate sequences in the second candidate-sequence set to generate a third set of one or more candidate sequences, wherein the third candidate-sequence set is obtained from the second candidate-sequence set by using the determined valid amino-acid sequences to substitute the one or more AACs and then discarding any candidate sequence with an undetermined AAC;

if the third candidate-sequence set consists of a single candidate sequence, then assigning the single candidate sequence in the third candidate-sequence set as one estimate of the peptide sequence, else selecting one or more candidate sequences from the third candidate-sequence set to form a fourth set of one or more candidate sequences such that the one or more candidate sequences in the fourth candidate-sequence set are more probable to be the peptide sequence than non-selected candidate sequences in the third candidate-sequence set; and if the fourth candidate-sequence set consists of a single candidate sequence, then assigning the single candidate sequence in the fourth candidate-sequence set as one estimate of the peptide sequence, else assigning plural candidate sequences in the fourth candidate-sequence set as estimates of the peptide sequence.

2. The method of claim 1, wherein the preprocessing of the raw data to yield the preprocessed data comprises:

dividing a set of mass/charge ratios of the raw data into a plurality of subsets such that an individual subset consists of mass/charge ratios of isotopes of a fragment of the data-encoded peptide, an individual mass/charge ratio having a signal peak in the experimental spectrum, the isotopes of the fragment having a same charge of positive integer value;

computing a monoisotopic mass of the fragment for the individual subset;

computing an intensity of the fragment according to the raw data and the mass/charge ratios in the individual subset; and generating the preprocessed data, wherein:

the preprocessed data includes a plurality of masses and a plurality of intensities, wherein the plurality of masses is formed with the monoisotopic mass of the fragment for the individual subset, and wherein an individual mass is associated with a corresponding intensity; and the preprocessed data further includes a first mass set of putative b-ions and a second mass set of putative y-ions for the experimental spectrum, wherein the first and second mass sets are generated by distributing respective masses in the plurality of masses into the first and second mass sets.

3. The method of claim 2, wherein the identifying of the first candidate-sequence set from the spectrum graph further comprises the steps of:

(a) sorting the plurality of masses in a descending order of corresponding intensities of respective masses to thereby form an ordered sequence of masses, wherein the ordered sequence of masses ranks the plurality of masses with a highest-ranking mass being associated with a highest corresponding intensity;

(b) given a selected mass and a selected number of higher-ranking masses in the ordered sequence of masses, identifying one or more highest-intensity-based tags in the spectrum graph, wherein an individual highest-intensity-based tag is a partial sequence consisting of a first amino acid having the selected mass and a plurality of remaining amino acids each having a mass selected from the selected number of higher-ranking masses;

(c) processing the one or more highest-intensity-based tags, wherein processing the individual highest-intensity-based tag comprises:

determining a prefix and a suffix for the individual highest-intensity-based tag;

if the prefix and suffix are successfully determined, then combining the prefix, the individual highest-intensity-based tag and the suffix to form a new candidate sequence; and allocating the new candidate sequence to the first candidate-sequence set;

(d) sequentially using successive values in a strictly decreasing sequence of values as the selected number of higher-ranking masses to repeat the steps (b) and (c) until the first candidate-sequence set is not empty or the strictly decreasing sequence is exhausted; and (e) starting from the highest-ranking mass, sequentially using successive masses in the ordered sequence of masses as the selected mass to repeat the steps (b)-(d) until the first candidate-sequence set is not empty or a preselected number of higher-ranking masses in the ordered sequence of masses is reached.

4. The method of claim 3, wherein the determining of the prefix and suffix for the individual highest-intensity-based tag comprises:

identifying the prefix as a first path that is valid and that has a longest length in the spectrum graph, wherein:

the first path connects a head amino acid and a head of the individual highest-intensity-based tag;

one or more first amino acid combinations (AACs) with a total length at most a first maximum length are allowable to be present in the identified first path;

if a parent ion peak identified in the experimental spectrum has a charge of value 2, then the first maximum length is set as $L_{p1}$; and if the charge of the parent ion peak is of value 3, then the first maximum length is initially set as $L_{p1}$ in finding the first path, and is relaxed to $L_{p2}$ in response to failure of finding the first path under the first maximum length being $L_{p1}$, where $L_{p2} > L_{p1}$; and identifying the suffix as a second path that is valid and that has a longest length in the spectrum graph, wherein:

the second path connects a tail of the individual highest-intensity-based tag and a tail amino acid;

one or more second AACs with a total length at most a second maximum length are allowable to be present in the identified second path;

if the charge of the parent ion peak is of value 2, then the second maximum length is set as $L_{s1}$; and if the charge of the parent ion peak is of value 3, then the second maximum length is initially set as $L_{s1}$ in finding the second path, and is relaxed to $L_{s2}$ in response to failure of finding the second path under the second maximum length being $L_{s1}$, where $L_{s2} > L_{s1}$.

5. The method of claim 1, wherein the identifying of the first candidate-sequence set from the spectrum graph further comprises:

if a parent ion peak identified in the experimental spectrum has a charge of value 2, then identifying an individual candidate sequence in the first candidate-sequence set via searching over the second mass set; and if the charge of the parent ion peak is of value 3, then identifying the individual candidate sequence in the first candidate-sequence set via searching over the first and second mass sets.

6. The method of claim 1, wherein the selecting of the one or more candidate sequences from the first candidate-sequence set to form the second candidate-sequence set comprises:

selecting one or more candidate sequences with a longest length of consecutive amino acids among the candidate sequences in the first candidate-sequence set to form a fifth candidate-sequence set;

if the fifth candidate-sequence set consists of a single candidate sequence, then assigning the fifth candidate-sequence set to be the second candidate-sequence set, else selecting one or more candidate sequences with a largest number of amino acids among plural candidate sequences in the fifth candidate-sequence set to form a sixth candidate-sequence set;

if the sixth candidate-sequence set consists of a single candidate sequence, then assigning the sixth candidate-sequence set to be the second candidate-sequence set, else selecting one or more candidate sequences with a smallest match error among plural candidate sequences in the sixth candidate-sequence set to form a seventh candidate-sequence set;

if the seventh candidate-sequence set consists of a single candidate sequence, then assigning the seventh candidate-sequence set to be the second candidate-sequence set, else selecting one or more candidate sequences with a highest average intensity value of retrieved amino acids among plural candidate sequences in the seventh candidate-sequence set to form an eighth candidate-sequence set; and if the eighth candidate-sequence set consists of a single candidate sequence, then assigning the eighth candidate-sequence set to be the second candidate-sequence set, else selecting one or more candidate sequences with a highest number of occurrences for different ion types with different offsets among plural candidate sequences in the eighth candidate-sequence set to form the second candidate-sequence set.

7. The method of claim 1, wherein the selecting of one or more candidate sequences from the third candidate-sequence set to form the fourth candidate-sequence comprises:

selecting, from the third candidate-sequence set, one or more candidate sequences with a largest number of amino acids among the determined valid amino-acid sequences to form a ninth candidate-sequence set; and if the ninth candidate-sequence set consists of a single candidate sequence, then assigning the ninth candidate-sequence set to be the fourth candidate-sequence set, else selecting, from the ninth candidate-sequence set, one or more candidate sequences with a smallest match error among the determined valid amino-acid sequences to form the fourth candidate-sequence set.

8. The method of claim 1, wherein the identifying of the first candidate-sequence set from the spectrum graph further comprises:

identifying one or more paths that are valid and that have a longest length in the spectrum graph, wherein a valid path begins at a head vertex, and ends at a tail vertex with a mass of the data-encoded peptide;

using each of the identified one or more paths to generate a new candidate sequence; and allocating the new candidate sequence to the first candidate-sequence set.

9. The method of claim 1, wherein the verifying of whether the individual peptide-sequence estimate is invalid comprises checking a length of the individual peptide-sequence estimate against a predetermined correct length of the peptide sequence.

10. The method of claim 1, wherein the verifying of whether the individual peptide-sequence estimate is invalid comprises performing order checking for amino acids "G" and "L" in the individual peptide-sequence estimate.

11. The method of claim 1, wherein the verifying of whether the individual peptide-sequence estimate is invalid comprises performing order checking based on order-checking bits carried in the data-encoded peptide.

12. A computer-implemented method for sequencing a data-encoded peptide from an experimental spectrum, raw data of the experimental spectrum being data of a histogram of intensity versus mass/charge ratio as originally obtained in analyzing the data-encoded peptide by mass spectrometry, the method comprising:

preprocessing the raw data for removing uninterpretable peaks to yield preprocessed data;

identifying, from a spectrum graph, a first set of one or more candidate sequences contending for a peptide sequence of the peptide, wherein the spectrum graph is formed according to the preprocessed data rather than the raw data for generating a fewer number of candidate sequences to thereby reduce a time cost in sequencing;

processing the first candidate-sequence set to estimate the peptide sequence;

after a set of one or more estimates of the peptide sequence is obtained, verifying whether an individual peptide-sequence estimate is invalid; and purging the set of one or more estimates of the peptide sequence to remove any peptide-sequence estimate found to be invalid;

wherein the preprocessing of the raw data to yield the preprocessed data comprises:

dividing a set of mass/charge ratios of the raw data into a plurality of subsets such that an individual subset consists of mass/charge ratios of isotopes of a fragment of the data-encoded peptide, an individual mass/charge ratio having a signal peak in the experimental spectrum, the isotopes of the fragment having a same charge of positive integer value;

computing a monoisotopic mass of the fragment for the individual subset;

computing an intensity of the fragment according to the raw data and the mass/charge ratios in the individual subset; and generating the preprocessed data, wherein:

the preprocessed data includes a plurality of masses and a plurality of intensities, wherein the plurality of masses is formed with the monoisotopic mass of the fragment for the individual subset, and wherein an individual mass is associated with a corresponding intensity; and the preprocessed data further includes a first mass set of putative b-ions and a second mass set of putative y-ions for the experimental spectrum, wherein the first and second mass sets are generated by distributing respective masses in the plurality of masses into the first and second mass sets;

and wherein the identifying of the first candidate-sequence set from the spectrum graph comprises the steps of:

(a) sorting the plurality of masses in a descending order of corresponding intensities of respective masses to thereby form an ordered sequence of masses, wherein the ordered sequence of masses ranks the plurality of masses with a highest-ranking mass being associated with a highest corresponding intensity;

(b) given a selected mass and a selected number of higher-ranking masses in the ordered sequence of masses, identifying one or more highest-intensity-based tags in the spectrum graph, wherein an individual highest-intensity-based tag is a partial sequence consisting of a first amino acid having the selected mass and a plurality of remaining amino acids each having a mass selected from the selected number of higher-ranking masses;

(c) processing the one or more highest-intensity-based tags, wherein processing the individual highest-intensity-based tag comprises:

determining a prefix and a suffix for the individual highest-intensity-based tag;

if the prefix and suffix are successfully determined, then combining the prefix, the individual highest-intensity-based tag and the suffix to form a new candidate sequence; and allocating the new candidate sequence to the first candidate-sequence set;

(d) sequentially using successive values in a strictly decreasing sequence of values as the selected number of higher-ranking masses to repeat the steps (b) and (c) until the first candidate-sequence set is not empty or the strictly decreasing sequence is exhausted; and (e) starting from the highest-ranking mass, sequentially using successive masses in the ordered sequence of masses as the selected mass to repeat the steps (b)-(d) until the first candidate-sequence set is not empty or a preselected number of higher-ranking masses in the ordered sequence of masses is reached.

13. The method of claim 12, wherein the determining of the prefix and suffix for the individual highest-intensity-based tag comprises:

identifying the prefix as a first path that is valid and that has a longest length in the spectrum graph, wherein:

the first path connects a head amino acid and a head of the individual highest-intensity-based tag;

one or more first amino acid combinations (AACs) with a total length at most a first maximum length are allowable to be present in the identified first path;

if a parent ion peak identified in the experimental spectrum has a charge of value 2, then the first maximum length is set as $L_{p1}$; and if the charge of the parent ion peak is of value 3, then the first maximum length is initially set as $L_{p1}$ in finding the first path, and is relaxed to $L_{p2}$ in response to failure of finding the first path under the first maximum length being $L_{p1}$, where $L_{p2} > L_{p1}$;

and identifying the suffix as a second path that is valid and that has a longest length in the spectrum graph, wherein:

the second path connects a tail of the individual highest-intensity-based tag and a tail amino acid;

one or more second AACs with a total length at most a second maximum length are allowable to be present in the identified second path;

if the charge of the parent ion peak is of value 2, then the second maximum length is set as $L_{s1}$; and if the charge of the parent ion peak is of value 3, then the second maximum length is initially set as $L_{s1}$ in finding the second path, and is relaxed to $L_{s2}$ in response to failure of finding the second path under the second maximum length being $L_{s1}$, where $L_{s2} > L_{s1}$.

14. The method of claim 12, wherein the identifying of the first candidate-sequence set from the spectrum graph further comprises:

if a parent ion peak identified in the experimental spectrum has a charge of value 2, then identifying an individual candidate sequence in the first candidate-sequence set via searching over the second mass set; and if the charge of the parent ion peak is of value 3, then identifying the individual candidate sequence in the first candidate-sequence set via searching over the first and second mass sets.

15. The method of claim 12, wherein the identifying of the first candidate-sequence set from the spectrum graph further comprises:

identifying one or more paths that are valid and that have a longest length in the spectrum graph, wherein a valid path begins at a head vertex, and ends at a tail vertex with a mass of the data-encoded peptide;

using each of the identified one or more paths to generate a new candidate sequence; and allocating the new candidate sequence to the first candidate-sequence set.

16. The method of claim 12, wherein the verifying of whether the individual peptide-sequence estimate is invalid comprises checking a length of the individual peptide-sequence estimate against a predetermined correct length of the peptide sequence.

17. The method of claim 12, wherein the verifying of whether the individual peptide-sequence estimate is invalid comprises performing order checking for amino acids "G" and "L" in the individual peptide-sequence estimate.

18. The method of claim 12, wherein the verifying of whether the individual peptide-sequence estimate is invalid comprises performing order checking based on order-checking bits carried in the data-encoded peptide.

* * * * *